(12) United States Patent
McLaughlin et al.

(10) Patent No.: US 10,556,928 B2
(45) Date of Patent: Feb. 11, 2020

(54) STABILIZED PEPTOID-PEPTIDE HYBRIDS AND USES THEREOF

(71) Applicants: H. LEE MOFFITT CANCER CENTER AND RESEARCH INSTITUTE, INC., Tampa, FL (US); UNIVERSITY OF SOUTH FLORIDA, Tampa, FL (US)

(72) Inventors: Mark McLaughlin, Morgantown, WV (US); Amod A. Sarnaik, Tampa, FL (US)

(73) Assignees: H. LEE MOFFITT CANCER CENTER AND RESEARCH INSTITUTE, INC., Tampa, FL (US); UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 16/157,174

(22) Filed: Oct. 11, 2018

(65) Prior Publication Data

US 2019/0040104 A1     Feb. 7, 2019

Related U.S. Application Data

(63) Continuation of application No. 15/300,451, filed as application No. PCT/US2015/023515 on Mar. 31, 2015, now Pat. No. 10,197,575.

(60) Provisional application No. 61/973,052, filed on Mar. 31, 2014.

(51) Int. Cl.
*G01N 33/68* (2006.01)
*C07K 7/64* (2006.01)
*C07K 14/00* (2006.01)

(52) U.S. Cl.
CPC ............. *C07K 7/64* (2013.01); *C07K 14/00* (2013.01); *G01N 33/68* (2013.01); *G01N 33/6842* (2013.01); *G01N 33/6845* (2013.01); *Y02A 50/58* (2018.01)

(58) Field of Classification Search
None
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 5,167,649 A | 12/1992 | Zook | |
| 5,811,515 A | 9/1998 | Grubbs et al. | |
| 6,960,648 B2 | 11/2005 | Bonny | |
| 7,192,713 B1 | 3/2007 | Verdine et al. | |
| 7,723,469 B2 | 5/2010 | Walensky et al. | |
| 7,786,072 B2 | 8/2010 | Verdine et al. | |
| 8,198,405 B2 | 6/2012 | Walensky et al. | |
| 8,324,428 B2 | 12/2012 | Verdine et al. | |
| 8,592,377 B2 | 11/2013 | Verdine et al. | |
| 8,853,149 B2 | 10/2014 | Hazlehurst et al. | |
| 10,011,635 B2 | 7/2018 | Hazlehurst et al. | |
| 10,059,740 B2 | 8/2018 | Hazlehurst et al. | |
| 2002/0035243 A1 | 3/2002 | Imfeld et al. | |
| 2002/0120100 A1 | 8/2002 | Bonny | |
| 2003/0032594 A1 | 2/2003 | Bonny | |
| 2015/0017259 A1 | 1/2015 | Hazlehurst et al. | |
| 2015/0071918 A1 | 3/2015 | McLaughlin et al. | |
| 2015/0105328 A1 | 4/2015 | McLaughlin et al. | |
| 2016/0229892 A1 | 8/2016 | Hazlehurst et al. | |
| 2017/0202902 A1 | 7/2017 | McLaughlin et al. | |

FOREIGN PATENT DOCUMENTS

| WO | WO 2011/115688 | 9/2011 |
|---|---|---|
| WO | WO 2011/156003 | 12/2011 |
| WO | WO 2013/170066 | 11/2013 |
| WO | WO 2013/192628 | 12/2013 |
| WO | WO 2015/048477 | 4/2015 |
| WO | WO 2015/200828 | 12/2015 |

OTHER PUBLICATIONS

Dooley, C.T. and Houghten, R.A. "Synthesis and Screening of Positional Scanning Combinatorial Libraries" In: Cabilly, S. (Eds) Combinatorial Peptide Library Protocols. Methods in Molecular Biology. Humana Press. 1998, vol. 87, pp. 13-24; Abstract.

Messeguer et al. "Synthesis of a positional scanning library of pentamers of N-alkylglycines assisted by microwave activation and validation via the identification of trypsin inhibitors" *Journal of Combinatorial Chemistry*, 2008, vol. 10, No. 6, pp. 974-980.

Shankaramma et al. "A family of macrocyclic antibiotics with a mixed peptide-peptoid beta-hairpin backbone conformation" *Chemical Communications*, 2003, vol. 15, pp. 1842-1843.

Zuckermann et al. "Peptoids as potential therapeutics" *Current Opinion Molecular Therapeutics*, 2009, vol. 11, No. 3, pp. 299-307.

*Primary Examiner* — Christopher M Gross
(74) *Attorney, Agent, or Firm* — Saliwanchik, Lloyd & Eisenschenk

(57) ABSTRACT

The current invention pertains to stabilized peptoids or peptoid-peptide hybrids. The peptoids or peptoid-peptide hybrids are stabilized by side chain-side to side chain linkages and/or backbone cyclization. The current invention also provides a positional library scanning method for identification of peptoids or peptoid-peptide hybrids having a desired biological activity.

12 Claims, 11 Drawing Sheets

Stapled Peptoid-Peptide with Crosslinker 1

Stapled Peptoid-Peptide with Crosslinker 2

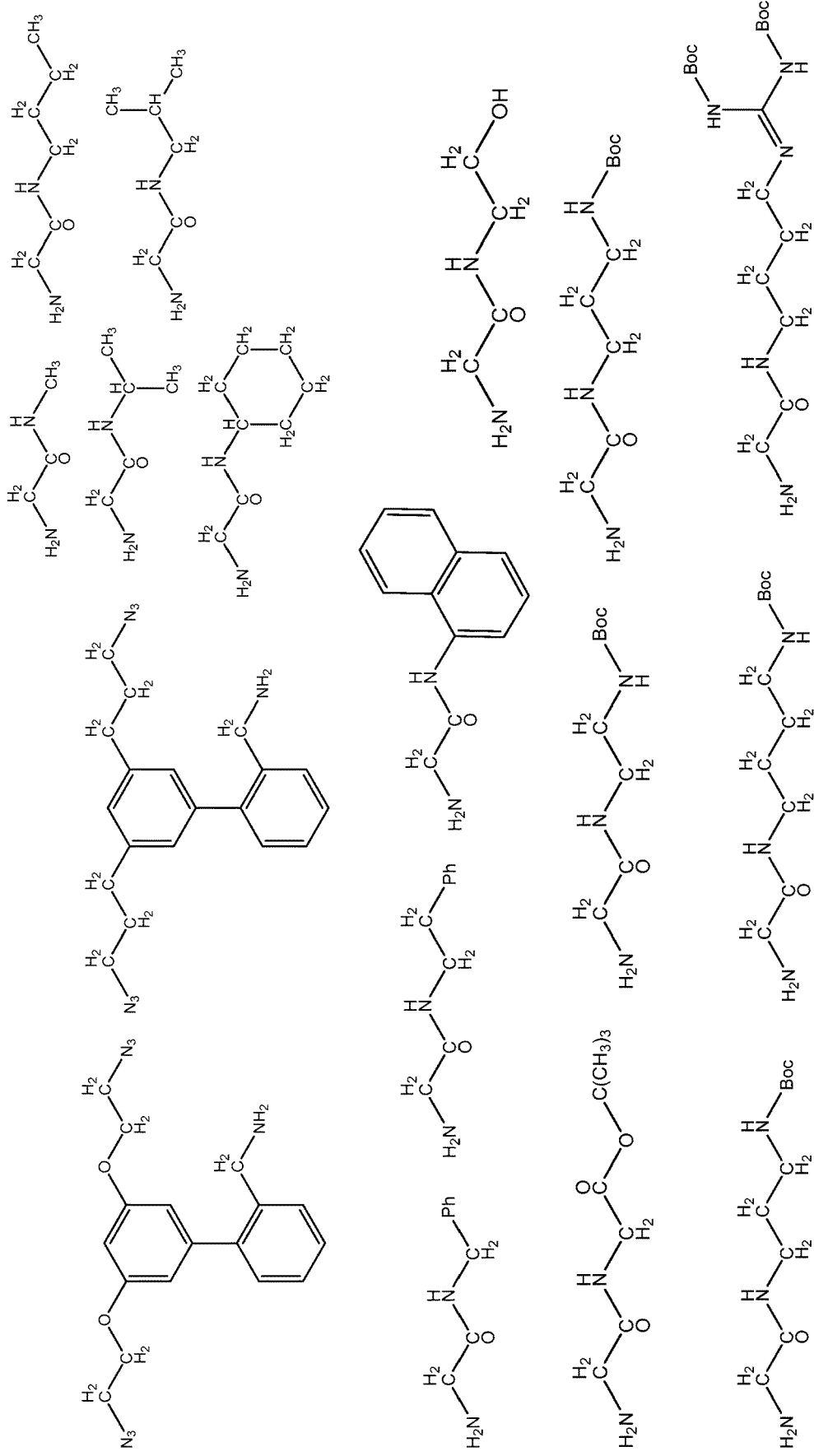
FIG. 9  Additional Variable R₁-R₄ Side Chains

STABILIZED PEPTOID-PEPTIDE HYBRIDS AND USES THEREOF

CROSS-REFERENCE TO RELATED APPLICATIONS

The present application is a continuation of U.S. application Ser. No. 15/300,451, filed Sep. 29, 2016, which is the National Stage of International Application Number PCT/US2015/023515, filed Mar. 31, 2015, which claims the benefit of U.S. Provisional Application Ser. No. 61/973,052, filed Mar. 31, 2014, each of which is hereby incorporated by reference herein in its entirety, including any figures, tables, nucleic acid sequences, amino acid sequences, or drawings.

BACKGROUND OF THE INVENTION

Peptoids, comprised of poly N-substituted glycines, are an attractive substitute for peptides as therapeutics because they can confer higher stability and resistance to peptidase enzymes and there are easier to structurally diversify due to the much greater variability of peptoid sub-monomer side chains. Peptoid-peptide hybrids can potentially provide the benefits of peptoids with the self-assembled secondary structure advantages of peptides. Cyclic peptoid-peptide hybrids can adopt a beta-hairpin-like secondary structure. This cyclic beta-hairpin-like design results from the alternation of the peptide-peptoid sub-units in two antiparallel beta-strands.

Peptides stabilized by cross linking between the amino acid side chains, referred to herein as "stapled peptides," have become an important tool in the development of protein-protein interaction inhibitors. Stapled peptides have improved cell penetration, enhanced specificity and stability, low cost of manufacturing, and shorter time duration from concept to drug development. However, stapled peptides do not provide various benefits afforded by peptoids and peptoid-peptide hybrids, such as easy diversification of the side chains and easier placement of side chains that can be stapled together to stabilize a preferred structure.

BRIEF SUMMARY OF THE INVENTION

Cyclic peptoid-peptide hybrids can have the chemical structure shown in formula I below:

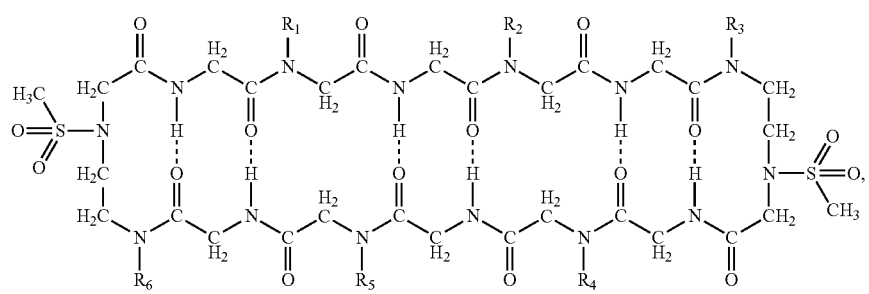

wherein $R_1$-$R_6$ are independently organic groups.

Additional examples of peptoid-peptide hybrids are described in U.S. Provisional Patent Application No. 61/663,325 and PCT Application Number PCT/US2013/47417, published as WO/2013/192628 (entitled "Peptoid-Peptide Hybrids and Their Use"). The contents of the Provisional Patent Application and the PCT Application Publication are incorporated herein by reference in their entireties.

In an embodiment of the invention, the cyclic peptoid-peptide hybrids have the chemical structure shown in formula II:

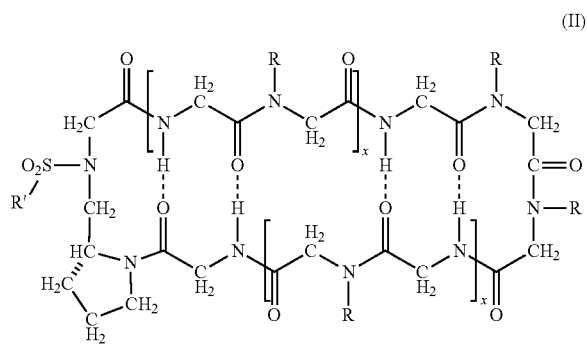

or a pharmaceutically acceptable salt or hydrate thereof, wherein R groups are independently organic groups, R' is an organic group, or an organic bridging group to a resin or other substrate, and x is 1 to 10.

In an embodiment of the invention, the cyclic peptoid-peptide hybrids have the chemical structure shown in formula III:

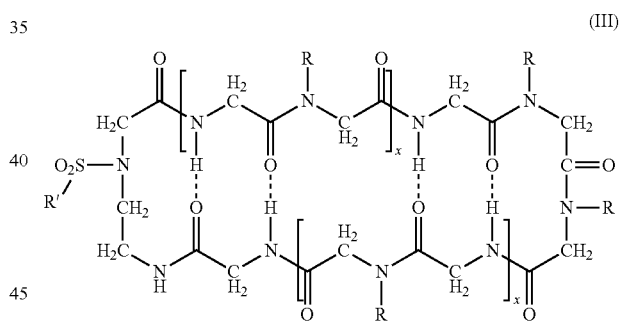

or a pharmaceutically acceptable salt or hydrate thereof, wherein R groups are independently organic groups, R' is an organic group, or an organic bridging group to a resin or other substrate, and x is 1 to 10.

In an embodiment of the invention, the cyclic peptoid-peptide hybrids have the chemical structure shown in formula IV:

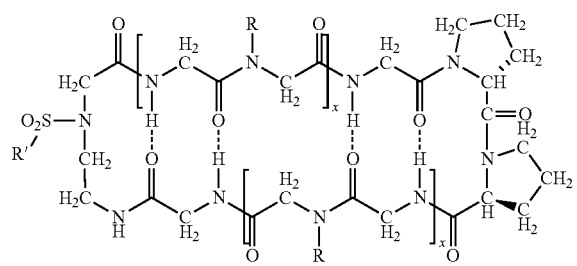

(IV)

or a pharmaceutically acceptable salt or hydrate thereof, wherein R groups are independently organic groups, R' is an organic group, or an organic bridging group to a resin or other substrate, and x is 1 to 10.

In an embodiment of the invention, the cyclic peptoid-peptide hybrids have the chemical structure shown in formula V:

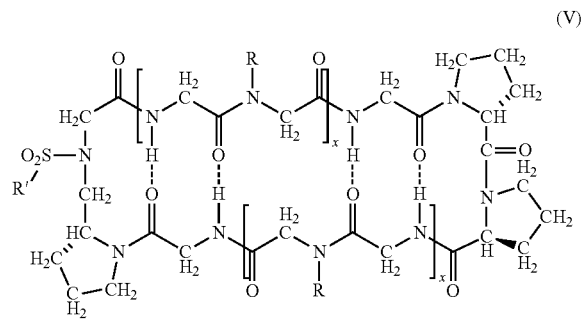

(V)

or a pharmaceutically acceptable salt or hydrate thereof, wherein, R groups are independently organic groups; R' is an organic group, or an organic bridging group to a resin or other substrate, and x is 1 to 10.

In an embodiment of the invention, the cyclic peptoid-peptide hybrids have the chemical structure shown in formula VI:

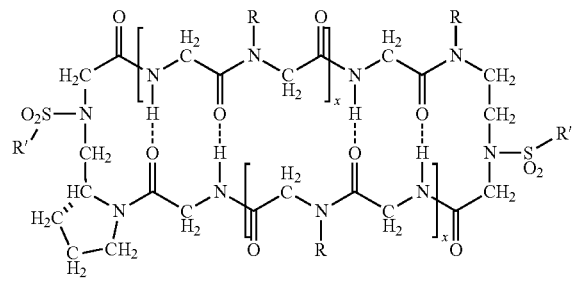

(VI)

or a pharmaceutically acceptable salt or hydrate thereof, wherein R groups are independently organic groups, R' is independently an organic group, or an organic bridging group to a resin or other substrate, and x is 1 to 10.

In an embodiment of the invention, the cyclic peptoid-peptide hybrids have the chemical structure shown in formula VII:

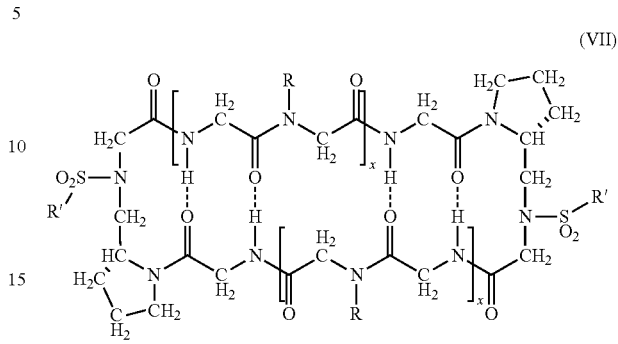

(VII)

or a pharmaceutically acceptable salt or hydrate thereof, wherein R groups are independently organic groups, R' is independently an organic group, or an organic bridging group to a resin or other substrate, and x is 1 to 10.

In an embodiment of the invention, the cyclic peptoid-peptide hybrids have the chemical structure shown in formula VIII:

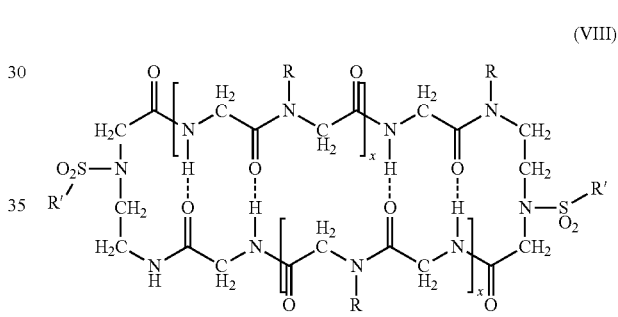

(VIII)

or a pharmaceutically acceptable salt or hydrate thereof, wherein R groups are independently organic groups, R' is independently an organic group, or an organic bridging group to a resin or other substrate, and x is 1 to 10.

In an embodiment of the invention, the cyclic peptoid-peptide hybrids have the chemical structure shown in formula IX:

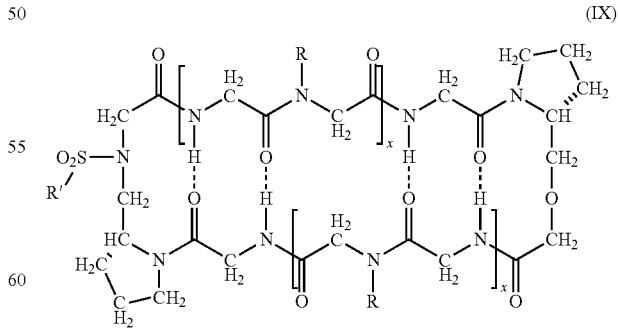

(IX)

or a pharmaceutically acceptable salt or hydrate thereof, wherein R groups are independently organic groups, R' is an organic group, or an organic bridging group to a resin or other substrate, and x is 1 to 10.

In an embodiment of the invention, the cyclic peptoid-peptide hybrids have the chemical structure shown in formula X:

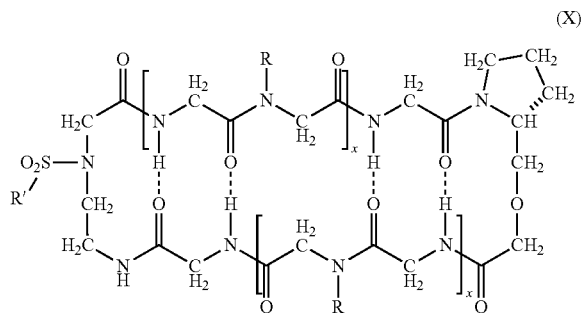

or a pharmaceutically acceptable salt or hydrate thereof, wherein R groups are independently organic groups, R' is an organic group, or an organic bridging group to a resin or other substrate, and x is 1 to 10.

In an embodiment of the invention, R groups of at least two adjacent peptoid-glycine sequences are 4-piperidinyl groups, for example, a compound of Formula II where x is 2:

whereas, such peptoid-peptide hybrids are herein referred to as "stapled peptoid-peptide hybrids."

The current invention also provides a positional library scanning method for identification of peptoid or peptoid-peptide hybrid having a desired biological activity.

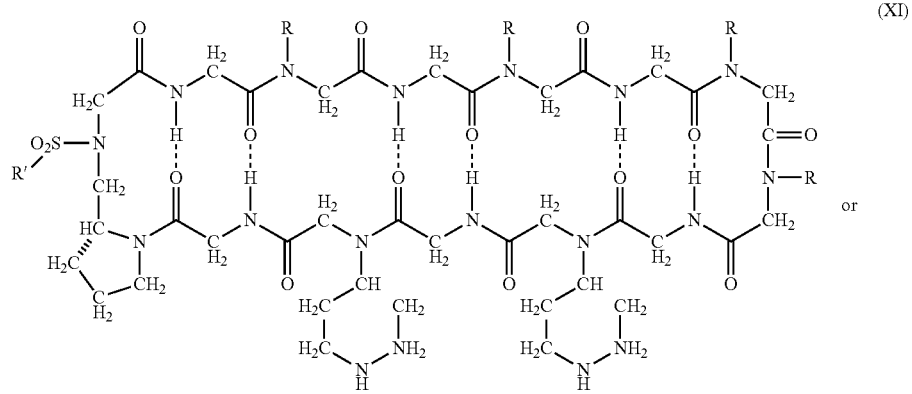

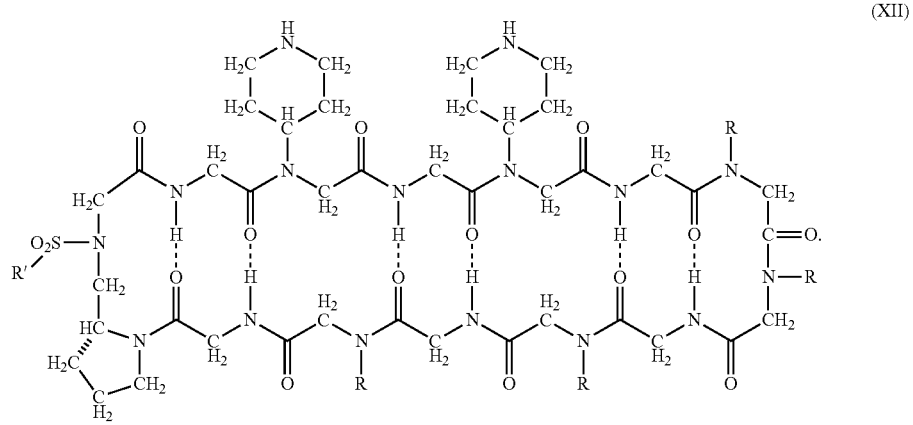

The current invention provides stabilized peptoids and stabilized peptoid-peptide hybrids. Without necessarily being bound by theory, stabilization is conferred by cross linking between the amino acid side chains, and/or the N-substitutions on glycines, and/or backbone cyclization. Such peptoids are referred to herein as "stapled peptoids;"

Figure 8:
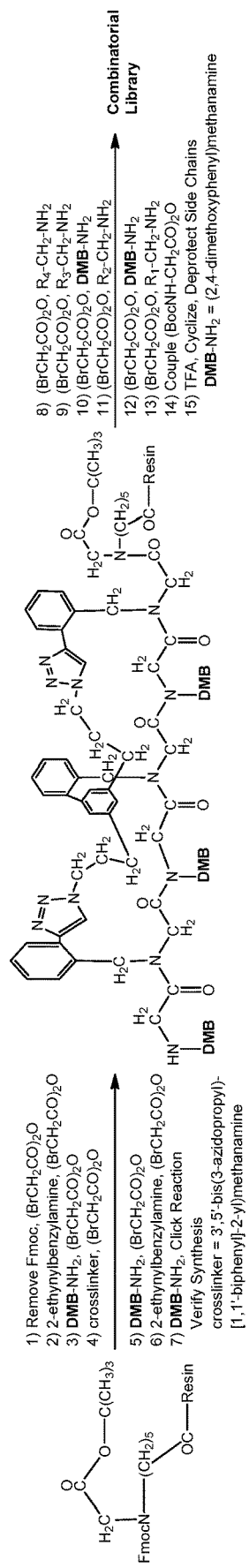

FIG. 8. Example of a reaction scheme for synthesis of a stapled peptoid-peptide with a cross-linker.

FIG. 9. Examples of variable side chains for stabilized peptoid and stabilized peptoid-peptide hybrids (shown attached to the N atom as primary amines), such as variables $R_1$-$R_4$ of the stapled peptoid-peptide hybrid of FIG. 1A, variable side chains of FIGS. 3-6, or R groups of formula I, formula II, formula III, formula IV, formula V, formula VI, formula VII, formula VIII, formula IX, formula X, formula XI, or formula XII.

DETAILED DESCRIPTION OF THE INVENTION

The current invention provides stabilized peptoid and stabilized peptoid-peptide hybrids. A scaffold based on peptoids was designed to produce a peptoid-peptide hybrid. The peptoid-peptide hybrid can be a cyclic peptoid-peptide hybrid. The cyclic peptoid-peptide hybrid has the hallmarks of an antiparallel beta-sheet dimer with at least one beta-turn promoter to help initiate the cyclic beta-hairpin-like fold. These scaffolds can be further stabilized by stapling. The stapled peptoid-peptide hybrid scaffolds have protein-like stability with a predictable secondary structure; however, they are more resistant to protease degradation compared to proteins or peptides.

As used herein, the term "peptoid" refers to an oligomer that usually has every amide of a glycine oligomer substituted with an R group, where the R is a methyl or a larger group. Peptoids thus cannot directly mimic the hydrogen bonding that proteins have to self-assemble into beta-sheet or into alpha-helix secondary structures. An oligoprolylproline sequence is both a peptoid and peptide in that it has an alpha-amino acid oligomer, but it is also substituted on every amide nitrogen. A peptide usually has a number of backbone amide hydrogens which allows some peptides to adopt secondary structures of beta-sheets or alpha-helices. The term "peptoid-peptide" is used to describe the alternation of backbone amide hydrogens with R group substituted peptoid-like groups that can mimic a beta-sheet along on strand edge of a sequence of a peptoid-peptide hybrid.

Stapling of peptoids or peptoid-peptide hybrids involves side chain-to-side chain linkages and/or backbone cyclization to stabilize the peptoids or the peptoid-peptide hybrids. Thus, the current invention extends the approach of stabilizing peptides using stabilized side chain linkages to stabilizing peptoids or peptoid-peptide hybrids.

For the purpose of the current invention, the term "side chain" includes a side chain on the amino acid as well as the moiety attached to the N atom of the N-substituted glycine.

Several possible side chain-to-side chain linkages (hereinafter referred to as intramolecular cross-linking) can be designed. The intramolecular cross-linking between the two sides chains of the peptoids or the peptoid-peptide hybrids of the current invention can be mediated through chemical reactions between the side chains which can also involve additional chemicals.

For example, the intramolecular cross-linking can be mediated through a chemical moiety, which is not a part of the side chains and wherein the side chains connect to each other via the chemical moiety. An example of the chemical moiety forming the intramolecular cross-linking is described in Example 2 and FIGS. 3-5.

In some embodiments of the invention, the intramolecular cross-link is established by the RCM (ring-closing metathesis) approach according Aileron or a Click reaction (e.g., Copper Catalyzed 3+2 cycloaddition) described in U.S. Pat. No. 5,811,515, which is incorporated herein by reference in its entirety. An example of intramolecular cross-linking mediated through the RCM approach is described in FIG. 6.

In a further embodiment of the invention, the intramolecular cross-linking between the two side chains is established by formation of a chemical bond, for example, through a condensation reaction, between the functional groups present on the side chains. A condensation reaction is a chemical reaction in which two molecules or moieties (functional groups) combine via a chemical bond and the reaction involves the loss of one or more smaller molecules. Examples of condensation reaction between the side chains that can be used in producing the intramolecular cross-linking according to the current invention are well known to a person of ordinary skill in the art and such embodiments are within the purview of the current invention.

Figure 1A:
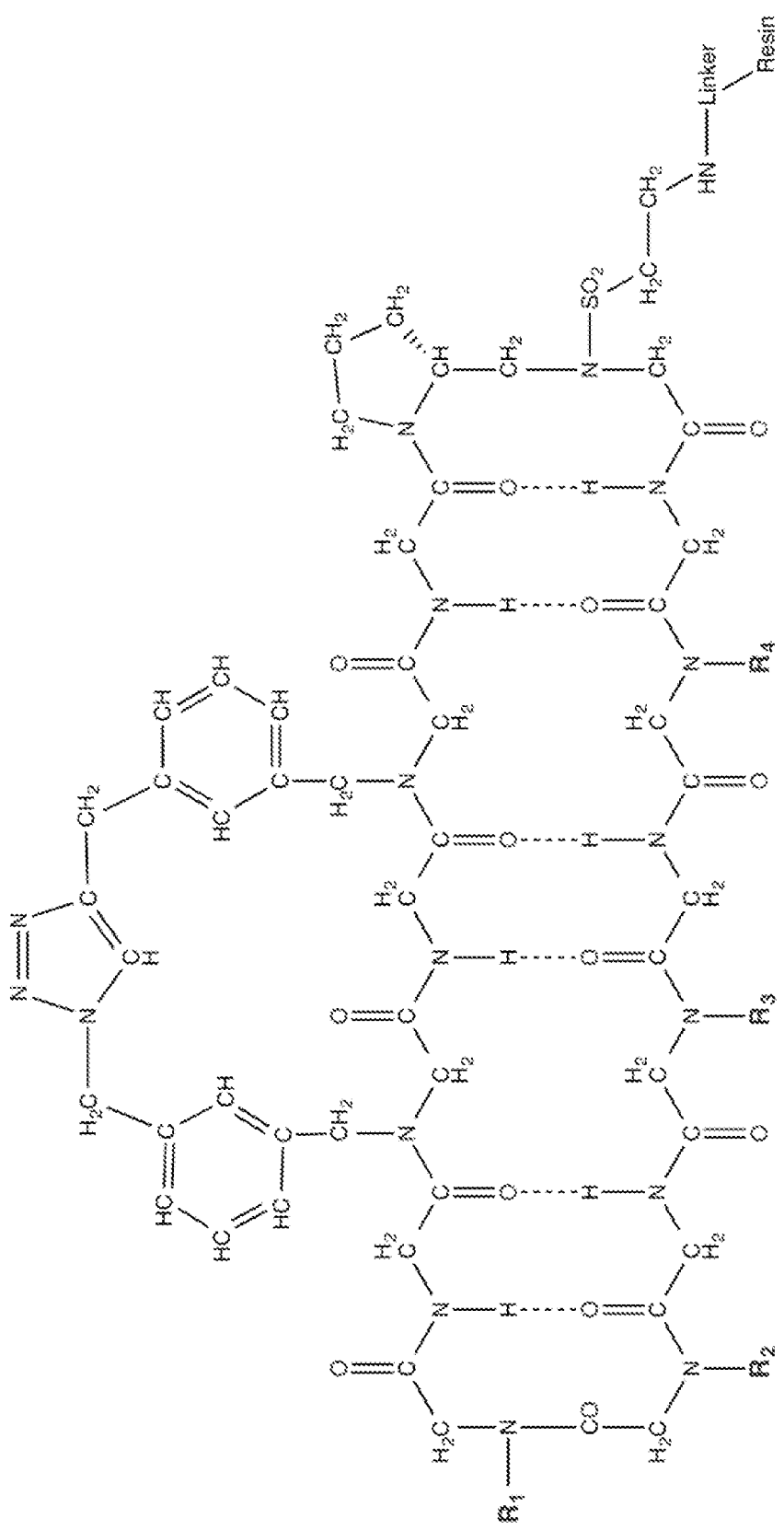
FIGS. 1A-1C. Examples of stapled peptoid-peptide hybrids.
Figure 1B:
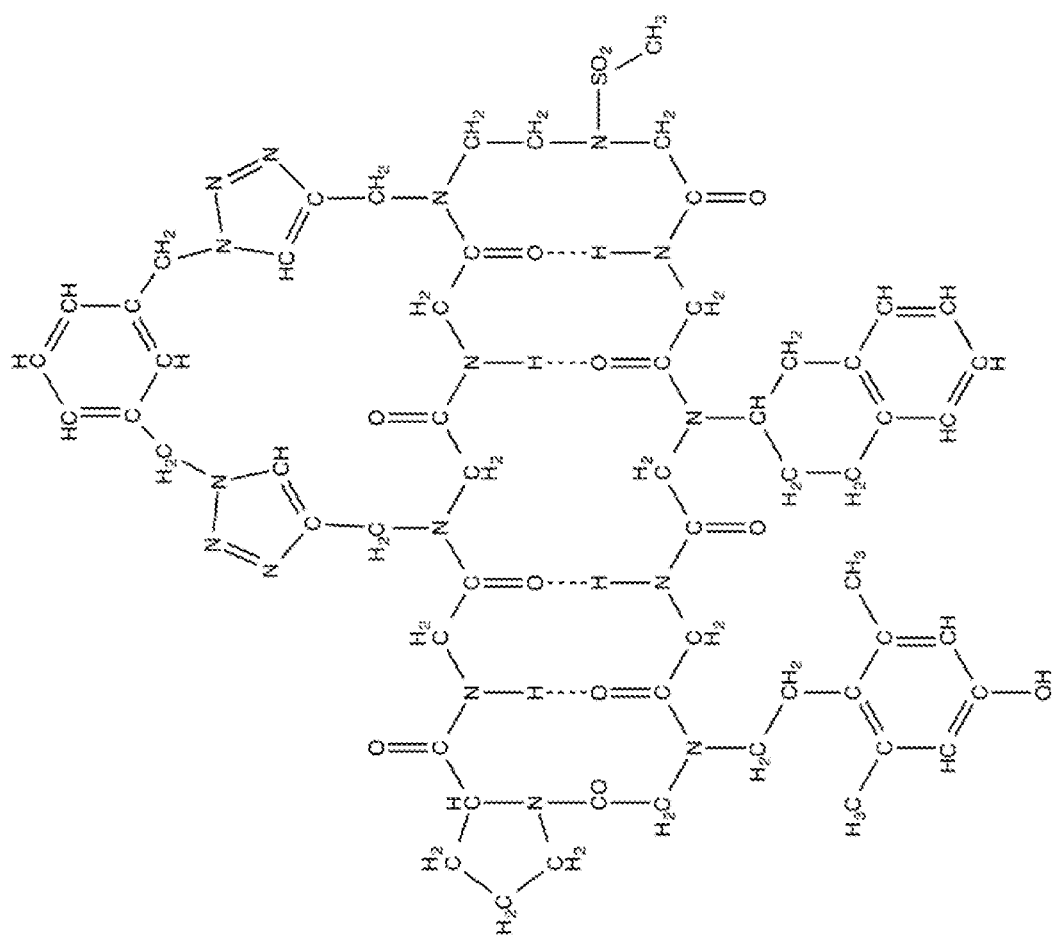
Figure 1C:
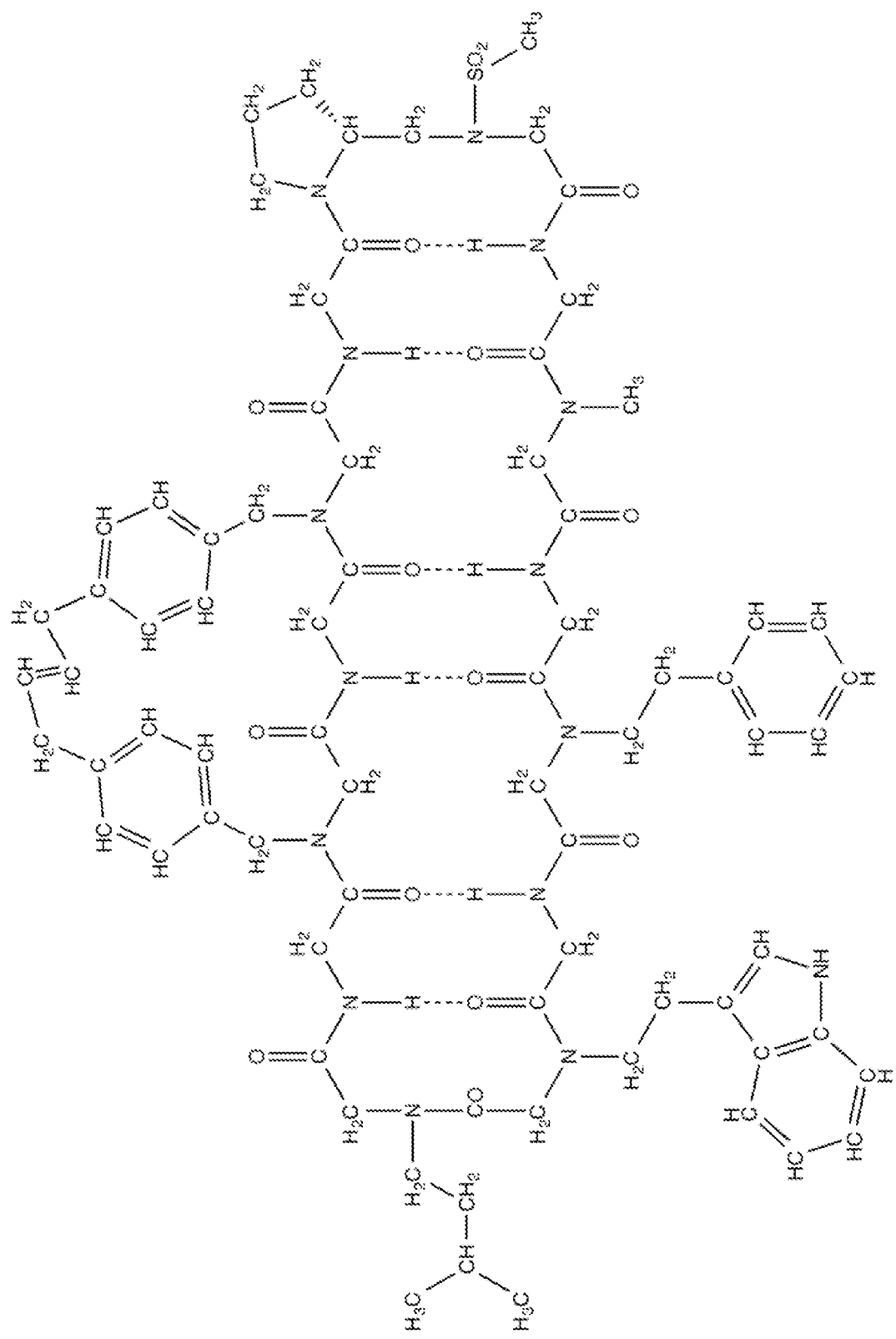

Additional examples of peptoids stapled with certain intramolecular cross-links are shown in FIGS. 1A-1C.

Additional examples of cross-links in peptides are disclosed in U.S. Pat. Nos. 8,592,377, 8,324,428, 8,198,405, 7,786,072, 7,723,469, 7,192,713, the contents of which are herein incorporated by reference in their entirety. A person of ordinary skill in the art can envision using various cross-links described in these patent documents in preparing the stapled peptoids and the stapled peptoid-peptide hybrids according to the current invention and such embodiments are within the purview of the current invention.

Accordingly, the current invention provides a stapled peptoid comprising a plurality of N-substituted glycines, wherein at least two of the N-substituted glycines are linked to each other by intramolecular cross-linking and wherein the length and geometry of the intramolecular cross-link provides stability to the peptoid.

The current invention also provides a stapled peptoid-peptide hybrid comprising a plurality of amino acids and plurality of N-substituted glycines, wherein at least two residues from the plurality of amino acids and the plurality of N-substituted glycines are linked to each other by an intramolecular cross-link and wherein the length and geometry of the intramolecular cross-link provides stability to the peptoid-peptide hybrid.

In one embodiment of the current invention two N-substituted glycine residues or two amino acid residues are linked to each other by a cross-link. In another embodiment, an N-substituted glycine residue is linked to an amino acid residue by a cross-link.

In a further embodiment of the invention, the stapled peptoid-peptide hybrid is a cyclic peptoid-peptide hybrid. A cyclic peptoid-peptide hybrid comprises a plurality of alternating peptoid-peptide sequences, each having at least one peptoid residue and an amino acid residue, wherein the peptoid-peptide sequences form at least two antiparallel beta-strands.

In one embodiment of the invention, the intramolecular cross-link is an all hydrocarbon cross-link.

In another embodiment of the invention, the peptoid or the peptoid-peptide hybrid comprises more than one intramolecular cross-link, for example, two, three, or four intramolecular cross-links.

In a particular embodiment, the cross-links are between two or more amino acid residues, or N-substituted glycine residues located on the same side of a beta sheet, thereby providing stability to the peptoid or peptoid-peptide hybrid. In a further embodiment, the intramolecular cross-links are between two or more amino acid residues, or N-substituted glycine residues located on the residues of a beta sheet, thereby providing stability to the peptoid or peptoid-peptide hybrid.

In certain embodiments of the current invention, the side chain can be selected from cyclic or acyclic, branched or unbranched, substituted cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene.

Additional examples of side chains and cross-links that can be applied in the current invention are disclosed, for example, in the U.S. Pat. No. 8,592,377 from column 37, line 26 to column 43, line 14; U.S. Pat. No. 8,198,405, column 3, line 54 to column 10, line 2 and column 25, line 14 to column 26, line 21; U.S. Pat. No. 7,786,072, column 5, line 44 to column 9, line 43 and column 11, line 16 to column 12, line 8; U.S. Pat. No. 7,723,469, column 5, line 30 to column 9, line 12 and column 24, line 60 to column 26, line 3; and U.S. Pat. No. 7,192,713, column 4, line 26 to column 9, line 45 and column 11, line 23 to column 12, line 18.

The stapled peptoids, peptoid-peptide hybrids, and stapled cyclic peptoid-peptide hybrids of the current invention can also further optionally contain substitutions in the side chains of the amino acid and/or the N-substituted glycine residues, wherein the substitutions in the side chains further stabilize the peptoids, peptoid-peptide hybrids, and cyclic peptoid-peptide hybrids. Non-limiting examples of various substitutions that could be used in the current invention are provided in Table 1. A person of ordinary skill in the art can envision additional examples of substitutions and such embodiments are within the purview of the current invention.

The current invention also provides a method of positional library scanning identification of peptoid or peptoid-peptide hybrid having a desired biological activity. The principle of positional library scanning was described by Richard A. Houghten et al. in Combinatorial Peptide Library Protocols, Series: Methods in Molecular Biology, Volume: 87, 1997, pp. 13-24, which is incorporated herein by reference in its entirety.

The peptoids or peptoid-peptide hybrids of the current invention can be screened for a desired biological activity, for example, the ability to specifically interact with a biomolecule. The biomolecule can be a polypeptide such as a protein or peptide, or a nucleic acid molecule, such as DNA or RNA. In one embodiment, the peptoids or peptoid-peptide hybrids of the current invention are screened for their ability to specifically bind to and inhibit the activity of a protein.

The peptoids or peptoid-peptide hybrids of the current invention can be screened to identify molecules that bind to tumor infiltrating lymphocytes (TILs) and promote their proliferation and activation. These compounds are advantageous over the use of antibodies for the same purpose because these peptoids or peptoid-peptide hybrids would potentially have a more favorable clearance rate and therefore may activate the patient's immune function for a relatively short time compared to antibodies that persist significantly longer.

Positional library scanning for designing peptoid-peptide hybrids is exceptionally useful due to the relatively small number of side chain positions. The diversity of the actual side chains is much greater in peptide side chains; however, the stabilized peptoids, peptoid-peptide hybrids and beta-hairpin-like peptoid-peptide scaffolds have enormous potential diversity due to the exceptionally high diversity of individual side chains that are easily accessible.

In an embodiment of the positional library of the current invention, a reservoir has a plurality of unique spots. The number of spots can vary between about 100 to about 500, about 150 to about 450, about 200 to about 400, about 250 to about 350, or about 300. In a specific embodiment of the positional library of the current invention, a reservoir has 345 unique spots.

In one embodiment, a molecular library that displays a mixture of "X" number of different substitutions in "N" number of different positions in a peptoid or peptoid-peptide hybrid is provided. When a particular substitution in one of the N positions is selected, the remaining positions display each of the $X^{(N-1)}$ possible combinations. This provides $NX^{(N-1)}$ different spots, which is much lesser than having to make an array containing every possible combination equaling $X^N$ spots.

Substantially reducing the number of spots required to be tested would reduce the materials required to screen the various combinations of N substitutions.

The positional scanning approach only displays about one-$X^{th}$ of a pure substance per spot, but the faster synthesis and screening of the positional library scanning makes up for this shortcoming. When a screen finds a hit, the hit can be prepared anew to verify its activity.

In a further embodiment, a molecular library that displays a mixture of "X" number of substitutions in either the $R_1$, or $R_2$, $R_3$ positions in the compound shown in FIG. 1A is provided. Once a substitution at $R_1$, $R_2$, or $R_3$ position is selected, the remaining, i.e. $R_1$ and $R_2$, $R_1$ and $R_3$, or $R_2$ and $R_3$ positions display each of the $X^2$ possible combinations. This provides $3X^2$ different spots, which is much less than having to make every possible combination equaling $X^3$ spots.

Substantially reducing the number of spots required to be tested would reduce the materials required to screen the various combinations of $R_1$, $R_2$, and $R_3$ substitutions. It should be understood that the variable groups at $R_1$, $R_2$, and $R_3$ are an exemplification. Compounds having more R positions (e.g., $R_4$, $R_5$, $R_6$, etc.), or less, are contemplated.

In some embodiments, the method of positional library scanning for identification of a peptoid or a peptoid-peptide hybrid having a desired biological activity, comprises the steps of:

a. producing a library of the peptoids having a core peptoid structure or the peptoid-peptide hybrids having a core peptoid-peptide structure, wherein the library consists of compounds having various combinations of N number of possible side chains on X number of possible substitution positions on the core peptoid or the core peptoid-peptide hybrid, b. producing a positional scanning library comprising an array of spots containing the peptoids or the peptoid-peptide hybrids, c. conducting an assay for the desired biological activity to identify one or more spots on the positional scanning library that display the desired biological activity, and d. further testing the compounds present in the spots that display the desired biological activity to identify the compounds having the desired biological activity.

In some embodiments, the desired biological activity is a specific interaction with a biomolecule, such as a polypeptide (e.g., protein) or a nucleic acid molecule (e.g., DNA or RNA).

In some embodiments, the library of peptoids comprises one or more of those described herein, e.g., formulas I-XII, FIGS. 1A-1C, and FIGS. 2-8.

As an alternative to the positional scanning approach, another aspect of the invention concerns a method for the analysis of a library of peptoid-peptide hybrids to identify a peptoid-peptide hybrid capable of binding to one or more biomolecules (for example, proteins in or on a cell), comprising the steps of:

a) providing an array comprising a combinatorial peptoid-peptide library, b) providing a first cell expressing one or more biomolecules of interest, wherein the first cell is labeled with a first label, c) providing a second cell not expressing the one or more biomolecules of interest, wherein the second cell is labeled with a second label distinguishable from the first label, d) contacting the first cell and the second cell to the combinatorial peptoid-peptide library, e) identifying, from the combinatorial peptoid-peptide library, the peptoid-peptide hybrid capable of binding to one or more biomolecules as indicated by the presence of the first label and the absence of the second label on the one or more positions on the array corresponding to the peptoid-peptide hybrid molecules.

In some embodiments, the method further comprises the step of labeling the first cell with the first label, and/or labeling the second cell with the second label.

Non-limiting examples of biomolecules can be a protein, nucleotide, lipid, polysaccharides. The protein can be a cytoplasmic protein or a cell surface protein. A cell surface protein can be a cell surface receptor protein. In one embodiment, the biomolecule is a cell surface protein.

In another embodiment, a peptoid-peptide library is screened for a molecule capable of binding to at least two biomolecules, for example, a protein and a lipid.

In a further embodiment, a peptoid-peptide library is screened for a molecule capable of binding to two cell surface proteins. In an even further embodiment, a peptoid-peptide library is screened for a molecule capable of binding 41BB receptor and TNF-β receptor.

In some embodiments, the first cell and the second cell differ only in the expression of the one or more proteins of interest. For example, the first cell can be modified to express the one or more proteins of interest, for example, by inserting genes which encode the one or more proteins; whereas, the second cell does not express the one or more proteins by virtue of the lack of genes or lack of expression of genes encoding the one or more proteins of interest.

The first label and the second label can be a fluorescent label, a quantum dot label (for example, red and blue), a radiolabel, an enzyme label, a chromophore, a chemiluminescent label or an antibody label. Additional examples of labels the can be used to label the first and the second cells are well known to a person of ordinary skill in the art and such embodiments are within the purview of the current invention.

In an embodiment, the first label is a quantum dot of a first color and the second label is a quantum dot of a second color. In one embodiment, the first label is a red quantum dot and the second label is a green quantum dot.

The array can be an array of spots of peptide-peptoid hybrids on a solid support. The array can also be peptide-peptoid hybrids in a multi-well format.

The method of detecting the binding of a first cell to a particular peptoid-peptide hybrid in a library depends on the type of label and the type of array used. A person of ordinary skill in the art can design various methods of detecting the binding of a first cell to one or more peptide-peptide hybrid in a library depending on the type of label and the type of array used.

An aspect of the invention includes a method for treating a disorder in a subject, comprising administering an effective amount of a pharmaceutical composition of the invention to the subject. The peptoids or peptoid-peptide hybrids of the current invention can be screened to bind any protein or nucleic acid; therefore, it should be appreciated that any disorder in which targeted killing, or targeted payloads, or interference with binding of two molecules is therapeutic, may be treated.

Various disorders may be treated, such as an oncological disorders (cancers), infections (e.g., from a pathogenic microorganism such as malaria), immunoregulatory abnormalities, such as autoimmune diseases and chronic inflammatory diseases. Examples of autoimmune or chronic inflammatory diseases include amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma. Other examples of immunoregulatory abnormality are bone marrow or organ transplant rejection or graft-versus-host disease. In some embodiments, the immunoregulatory abnormality is selected from the group consisting of: rejection brought about transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

The method may further comprise administering an effective amount of one or more other agents to the subject before, during, and/or after administration of the peptoids or peptoid-peptide hybrids of the current invention. For example, in the case of cancer, an anti-cancer agent can be administered.

Another aspect of the inventions concerns a method for inducing apoptosis or inhibiting the growth of a cell, comprising contacting the cell with an effective amount of a peptoid body in vitro or in vivo. In some embodiments, the cell is a cancer cell. In some embodiments, the cell is a pathogen-infected cell (e.g., a malaria-infected cell). The method may further comprise contacting the cell with one or more other agents before, during, and/or after contacting the cell with the peptoid or peptoid-peptide hybrid of the current invention. For example, in the case of a cancer cell, the cell may be contacted with one or more anti-cancer agents.

Peptoids or peptoid-peptide hybrids of the current invention also include pharmaceutically acceptable salts and hydrates of the subject compounds. Pharmaceutically acceptable salts include salts of the compounds of the invention, which are prepared with acids or bases, depending on the particular substituents found on the subject complexes described herein. Examples of pharmaceutically acceptable base addition salts include sodium, potassium, calcium, ammonium, or magnesium salt. Examples of pharmaceutically acceptable acid addition salts include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Pharmaceutically acceptable salts of compounds of the invention can be prepared using conventional techniques.

It will be appreciated by those skilled in the art that some of the compounds of the invention may contain one or more asymmetrically substituted carbon atoms, which can give rise to stereoisomers. It is understood that the invention extends to all such stereoisomers, including enantiomers, and diastereoisomers and mixtures, including racemic mixtures thereof.

The subject invention also concerns a packaged dosage formulation comprising in one or more containers at least one peptoid or peptoid-peptide hybrid of the current invention or composition of the invention. A packaged dosage formulation can optionally comprise in one or more containers a pharmaceutically acceptable carrier or diluent. A packaged dosage formulation can also optionally comprise, in addition to a peptoid or peptoid-peptide hybrid or a composition of the invention, other agents such as anti-cancer agents, including, but not limited to, chemotherapeutic drugs.

In vivo application of the peptoids or peptoid-peptide hybrids of the current invention, and compositions containing them, can be accomplished by any suitable method and technique presently or prospectively known to those skilled in the art. The subject compounds can be formulated in a pharmaceutically acceptable form and administered by any suitable route known in the art including, for example, oral, nasal, rectal, and parenteral routes of administration. As used herein, the term parenteral includes subcutaneous, intradermal, intravenous, intramuscular, intraperitoneal, and intrasternal administration, such as by injection. Administration of the compounds of the invention can be a single administration, or at continuous or distinct intervals as can be readily determined by a person skilled in the art.

The peptoids or peptoid-peptide hybrids of the current invention, and compositions comprising them, can also be administered utilizing liposome technology, slow release capsules, implantable pumps, and biodegradable containers. These delivery methods can, advantageously, provide a uniform dosage over an extended period. The compounds of the invention can also be administered in their salt derivative forms or crystalline forms.

Peptoids or peptoid-peptide hybrids of the current invention can be formulated according to known methods for preparing physiologically acceptable compositions. Formulations are described in detail in a number of sources, which are well known and readily available to those skilled in the art. For example, *Remington's Pharmaceutical Science* by E. W. Martin describes formulations, which can be used in connection with the subject invention. In general, the compositions of the subject invention will be formulated such that an effective amount of the compound is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional physiologically-acceptable carriers and diluents, which are known to those skilled in the art. Examples of carriers or diluents for use with the subject compounds include ethanol, dimethyl sulfoxide, glycerol, alumina, starch, saline, and equivalent carriers and diluents. To provide for the administration of such dosages for the desired therapeutic treatment, compositions of the invention will advantageously comprise between about 0.1% and 99%, and especially, 1 and 15% by weight of the total of one or more of the subject compounds based on the weight of the total composition including carrier or diluent.

Peptoids or peptoid-peptide hybrids of the current invention, and compositions comprising them, can be delivered to a cell (e.g., normal cell, cancerous cell, cell line) either through direct contact with the cell or via a carrier means. In some embodiments, the cell to which the compound or composition is contacted is a cancer cell of a type disclosed herein (e.g., Table 2). Carrier means for delivering compounds and compositions to cells are known in the art and include, for example, encapsulating the composition in a liposome moiety. Another means for delivery of compounds and compositions of the invention to a cell comprises attaching the compounds to a protein or nucleic acid that is targeted for delivery to the target cell. U.S. Pat. No. 6,960,648 and Published U.S. Patent Application Nos. 20030032594 and 20020120100 disclose amino acid sequences that can be coupled to another composition and that allows the composition to be translocated across biological membranes. Published U.S. Patent Application No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

Oncological disorders within the scope of the invention include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment with the present invention include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Examples of cancers that can be treated according to the present invention are listed in Table 2.

TABLE 2

| Examples of Cancer Types | |
| --- | --- |
| Acute Lymphoblastic Leukemia, Adult | Hairy Cell Leukemia Head and Neck Cancer |
| Acute Lymphoblastic Leukemia, Childhood | Hepatocellular (Liver) Cancer, Adult (Primary) |
| Acute Myeloid Leukemia, Adult | Hepatocellular (Liver) Cancer, Childhood (Primary) |
| Acute Myeloid Leukemia, Childhood | |
| Adrenocortical Carcinoma | Hodgkin's Lymphoma, Adult |
| Adrenocortical Carcinoma, Childhood | Hodgkin's Lymphoma, Childhood |
| AIDS-Related Cancers | Hodgkin's Lymphoma During Pregnancy |
| AIDS-Related Lymphoma | Hypopharyngeal Cancer |
| Anal Cancer | Hypothalamic and |
| Astrocytoma, Childhood Cerebellar | Visual Pathway Glioma, Childhood |
| Astrocytoma, Childhood Cerebral | |
| Basal Cell Carcinoma | Intraocular Melanoma |
| Bile Duct Cancer, Extrahepatic | Islet Cell Carcinoma |
| Bladder Cancer | (Endocrine Pancreas) |
| Bladder Cancer, Childhood | Kaposi's Sarcoma |

TABLE 2-continued

| Examples of Cancer Types | |
| --- | --- |
| Bone Cancer, Osteosarcoma/Malignant Fibrous Histiocytoma | Kidney (Renal Cell) Cancer Kidney Cancer, Childhood Laryngeal Cancer |
| Brain Stem Glioma, Childhood | Laryngeal Cancer, Childhood |
| Brain Tumor, Adult | Leukemia, Acute Lymphoblastic, Adult |
| Brain Tumor, Brain Stem Glioma, Childhood | Leukemia, Acute Lymphoblastic, Childhood |
| Brain Tumor, Cerebellar Astrocytoma, Childhood | Leukemia, Acute Myeloid, Adult |
| Brain Tumor, Cerebral Astrocytoma/Malignant Glioma, Childhood | Leukemia, Acute Myeloid, Childhood Leukemia, Chronic Lymphocytic |
| Brain Tumor, Ependymoma, Childhood | Leukemia, Chronic Myelogenous Leukemia, Hairy Cell |
| Brain Tumor, Medulloblastoma, Childhood | Lip and Oral Cavity Cancer Liver Cancer, Adult (Primary) |
| Brain Tumor, Supratentorial Primitive Neuroectodermal Tumors, Childhood | Liver Cancer, Childhood (Primary) Lung Cancer, Non-Small Cell Lung Cancer, Small Cell Lymphoma, AIDS-Related |
| Brain Tumor, Visual Pathway and Hypothalamic Glioma, Childhood | Lymphoma, Burkitt's Lymphoma, Cutaneous T-Cell, see Mycosis |
| Brain Tumor, Childhood Breast Cancer | Fungoides and Sézary Syndrome |
| Breast Cancer, Childhood | Lymphoma, Hodgkin's, Adult |
| Breast Cancer, Male | Lymphoma, Hodgkin's, Childhood |
| Bronchial Adenomas/Carcinoids, Childhood | Lymphoma, Hodgkin's During Pregnancy |
| Burkitt's Lymphoma | Lymphoma, Non-Hodgkin's, Adult |
| Carcinoid Tumor, Childhood | Lymphoma, Non-Hodgkin's, Childhood |
| Carcinoid Tumor, Gastrointestinal Carcinoma of Unknown Primary | Lymphoma, Non-Hodgkin's During Pregnancy |
| Central Nervous System Lymphoma, Primary | Lymphoma, Primary Central Nervous System |
| Cerebellar Astrocytoma, Childhood | |
| Cerebral Astrocytoma/Malignant Glioma, Childhood | Macroglobulinemia, Waldenström's Malignant Fibrous Histiocytoma of Bone/Osteosarcoma |
| Cervical Cancer | |
| Childhood Cancers | Medulloblastoma, Childhood |
| Chronic Lymphocytic Leukemia | Melanoma |
| Chronic Myelogenous Leukemia | Melanoma, Intraocular (Eye) |
| Chronic Myeloproliferative Disorders | Merkel Cell Carcinoma Mesothelioma, Adult Malignant |
| Colon Cancer | Mesothelioma, Childhood |
| Colorectal Cancer, Childhood | Metastatic Squamous Neck |
| Cutaneous T-Cell Lymphoma, see | Cancer with Occult Primary |
| Mycosis Fungoides and Sézary Syndrome | Multiple Endocrine Neoplasia Syndrome, Childhood |
| Endometrial Cancer | |
| Ependymoma, Childhood | Multiple Myeloma/Plasma |
| Esophageal Cancer | Cell Neoplasm |
| Esophageal Cancer, Childhood | Mycosis Fungoides |
| Ewing's Family of Tumors | Myelodysplastic Syndromes |
| Extracranial Germ Cell Tumor, Childhood | Myelodysplastic/Myeloproliferative Diseases |
| Extragonadal Germ Cell Tumor | Myelogenous Leukemia, Chronic |
| Extrahepatic Bile Duct Cancer | Myeloid Leukemia, Adult Acute |
| Eye Cancer, Intraocular Melanoma | Myeloid Leukemia, Childhood Acute Myeloma, Multiple |
| Eye Cancer, Retinoblastoma | Myeloproliferative |
| Gallbladder Cancer | Disorders, Chronic |
| Gastric (Stomach) Cancer | Nasal Cavity and Paranasal |
| Gastric (Stomach) Cancer, Childhood | Sinus Cancer Nasopharyngeal Cancer |
| Gastrointestinal Carcinoid Tumor | Nasopharyngeal Cancer, Childhood |
| Germ Cell Tumor, Extracranial, Childhood | Neuroblastoma Non-Hodgkin's Lymphoma, Adult |
| Germ Cell Tumor, Extragonadal | Non-Hodgkin's Lymphoma, Childhood |
| Germ Cell Tumor, Ovarian | |
| Gestational Trophoblastic Tumor | Non-Hodgkin's Lymphoma |
| Glioma, Adult | During Pregnancy |
| Glioma, Childhood Brain Stem | Non-Small Cell Lung Cancer |
| Glioma, Childhood Cerebral Astrocytoma | Oral Cancer, Childhood Oral Cavity Cancer, Lip and |
| Glioma, Childhood Visual Pathway and Hypothalamic | Oropharyngeal Cancer Osteosarcoma/Malignant Fibrous |
| Skin Cancer (Melanoma) | Histiocytoma of Bone |

TABLE 2-continued

Examples of Cancer Types

| | |
|---|---|
| Skin Carcinoma, Merkel Cell | Ovarian Cancer, Childhood |
| Small Cell Lung Cancer | Ovarian Epithelial Cancer |
| Small Intestine Cancer | Ovarian Germ Cell Tumor |
| Soft Tissue Sarcoma, Adult | Ovarian Low Malignant |
| Soft Tissue Sarcoma, Childhood | Potential Tumor |
| Squamous Cell Carcinoma, see Skin Cancer (non-Melanoma) | Pancreatic Cancer |
| | Pancreatic Cancer, Childhood |
| | Pancreatic Cancer, Islet Cell |
| Squamous Neck Cancer with Occult Primary, Metastatic | Paranasal Sinus and Nasal Cavity Cancer |
| | Parathyroid Cancer |
| Stomach (Gastric) Cancer | Penile Cancer |
| Stomach (Gastric) Cancer, Childhood | Pheochromocytoma |
| | Pineoblastoma and |
| Supratentorial Primitive Neuroectodermal Tumors, Childhood | Supratentorial Primitive Neuroectodermal Tumors, Childhood |
| T-Cell Lymphoma, Cutaneous, see Mycosis Fungoides and Sézary Syndrome | Pituitary Tumor |
| | Plasma Cell Neoplasm/ Multiple Myeloma |
| | Pleuropulmonary Blastoma |
| Testicular Cancer | Pregnancy and Breast Cancer |
| Thymoma, Childhood | Pregnancy and Hodgkin's Lymphoma |
| Thymoma and Thymic Carcinoma | Pregnancy and Non-Hodgkin's Lymphoma |
| Thyroid Cancer | |
| Thyroid Cancer, Childhood | Primary Central Nervous System Lymphoma |
| Transitional Cell Cancer of the Renal Pelvis and Ureter | |
| | Prostate Cancer |
| | Rectal Cancer |
| Trophoblastic Tumor, Gestational | Renal Cell (Kidney) Cancer |
| | Renal Cell (Kidney) Cancer, Childhood |
| Unknown Primary Site, Carcinoma of, Adult | |
| | Renal Pelvis and Ureter, Transitional Cell Cancer |
| Unknown Primary Site, Cancer of, Childhood | |
| | Retinoblastoma |
| Unusual Cancers of Childhood | Rhabdomyosarcoma, Childhood |
| Ureter and Renal Pelvis, Transitional Cell Cancer | |
| | Salivary Gland Cancer |
| Urethral Cancer | Salivary Gland Cancer, Childhood |
| Uterine Cancer, Endometrial | Sarcoma, Ewing's Family of Tumors |
| Uterine Sarcoma | Sarcoma, Kaposi's |
| Vaginal Cancer | Sarcoma, Soft Tissue, Adult |
| Visual Pathway and Hypothalamic Glioma, Childhood | Sarcoma, Soft Tissue, Childhood |
| | Sarcoma, Uterine |
| Vulvar Cancer | Sezary Syndrome |
| Waldenström's Macroglobulinemia | Skin Cancer (non-Melanoma) |
| Wilms' Tumor | Skin Cancer, Childhood |

For the treatment of oncological disorders, the peptides or peptoid-peptide hybrids of the current invention can be administered to a subject in need of treatment in combination with other anti-cancer substances and/or with anti-cancer treatments (such as radiation, photodynamic therapy, and surgical treatment) to remove a tumor. These other substances or treatments may be given at the same time as, or at different times from, the compounds and compositions of this invention. For example, the compounds of the present invention can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, anti-angiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site. The tumor "tumor" is inclusive of solid tumors and non-solid tumors. The peptoids or peptoid-peptide hybrids and compositions of the invention can be administered locally at the site of a tumor (e.g., by direct injection) or remotely.

As used herein, the terms "treat" or "treatment" refer to both therapeutic treatment and prophylactic or preventative measures, wherein the object is to prevent or slow down (lessen, or delay the onset of) an undesired physiological change or disorder, such as the development or spread of an oncological disorder (e.g., cancer), infection by a pathogenic microorganism (e.g., malaria), or immunoregulatory abnormality such as an autoimmune disease or chronic inflammatory disease. Thus, in some embodiments, the subject has an oncological disorder at the time of administration. In other embodiments, the subject does not have an oncological disorder at the time of administration, in which case the peptoids or peptoid-peptide hybrids of the current invention may be administered to prevent or delay onset of the oncologic disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. In some embodiments, the treatment methods include identifying the subject as having an oncologic disorder (e.g., cancer).

The amount of peptoids or peptoid-peptide hybrids administered to the subject may be an effective amount, e.g., a therapeutically effective amount. As used herein, the term "(therapeutically) effective amount" refers to an amount of an agent (e.g., a compound of the invention or other anti-cancer agent) effective to treat a disease or disorder in a mammal. In the case of cancer, the therapeutically effective amount of the agent may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve, to some extent, one or more of the symptoms associated with the cancer. To the extent the agent may prevent growth and/or kill existing cancer cells, it may be cytostatic and/or cytotoxic. For cancer therapy, efficacy can, for example, be measured by assessing the time to disease progression (TTP) and/or determining the response rate (RR).

The amount of peptoids or peptoid-peptide hybrids of the current invention administered to the subject may be a growth inhibitory amount. As used herein, the term "growth inhibitory amount" refers to an amount which inhibits growth of a target cell, such as a tumor cell, either in vitro or in vivo, irrespective of the mechanism by which cell growth is inhibited. In a preferred embodiment, the growth inhibitory amount inhibits growth of the target cell in cell culture by greater than about 20%, preferably greater than about 50%, most preferably greater than about 75% (e.g., from about 75% to about 100%).

The terms "cell" and "cells" are used interchangeably herein and are intended to include either a single cell or a plurality of cells unless otherwise specified.

As used herein, the term "anti-cancer agent" refers to a substance or treatment that inhibits the function of cancer cells, inhibits their formation, and/or causes their destruction in vitro or in vivo. Examples include, but are not limited to, cytotoxic agents (e.g., 5-fluorouracil, TAXOL) and anti-signaling agents (e.g., the PI3K inhibitor LY).

The methods of the present invention can be used with humans and other animal subjects. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses. In one embodiment, the subject is a human or non-human mammal.

While peptoids or peptoid-peptide hybrids of the current invention can be administered as isolated compounds, these compounds can also be administered as part of a pharmaceutical composition. The subject invention thus further provides compositions comprising one or more peptoids or peptoid-peptide hybrids of the current invention in association with at least one pharmaceutically acceptable carrier or diluent. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

The peptoids or peptoid-peptide hybrids of the current invention can be formulated according to known methods for preparing pharmaceutically useful compositions. Formulations are described in a number of sources which are well known and readily available to those skilled in the art. For example, *Remington's Pharmaceutical Science* (Martin 1995) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

The peptoids or peptoid-peptide hybrids of the current invention of the present invention include all hydrates and salts that can be prepared by those of skill in the art. Under conditions where the compounds and agents of the present invention are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of a compound or agent may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Therapeutic application of peptoids or peptoid-peptide hybrids of the current invention and compositions containing them can be accomplished by any suitable therapeutic method and technique presently or prospectively known to those skilled in the art. Further, compounds and agents of the invention have use as starting materials or intermediates for the preparation of other useful compounds and compositions.

Peptoids or peptoid-peptide hybrids of the current invention of the invention, and compositions thereof, may be locally administered at one or more anatomical sites, such as sites of unwanted cell growth (such as a tumor site or benign skin growth, e.g., injected or topically applied to the tumor or skin growth), sites of infection or other sites of diseased cells, optionally in combination with a pharmaceutically acceptable carrier such as an inert diluent. Compounds and agents of the invention, and compositions thereof, may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or as otherwise modifications of the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Peptoids or peptoid-peptide hybrids of the current invention and compositions of the invention, including pharmaceutically acceptable salts or hydrates thereof, can be administered by various routes, such as intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating one or more peptoids or peptoid-peptide hybrids of the current invention of the invention (with or without one or more additional anti-cancer agents) in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, peptoids or peptoid-peptide hybrids and compositions of the invention may be applied in as a liquid or solid. However, it will generally be desirable to administer them topically to the skin as compositions, in combination with a dermatologically acceptable carrier, which may be a solid or a liquid. Compounds and agents and compositions of the subject invention can be applied topically to a subject's skin to reduce the size (and may include complete removal) of malignant or benign growths, or to treat an infection site. Compounds and agents of the invention can be applied directly to the diseased site (e.g., the growth or infection site). Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the peptoids or peptoid-peptide hybrids and pharmaceutical compositions containing them can be determined by comparing their in vitro activity, and in vivo activity in animal models. Methods for the extrapolation of effective dosages in mice, and other animals, to humans are known to the art; for example, see U.S. Pat. No. 4,938,949.

The present invention also concerns pharmaceutical compositions comprising one or more peptoids or peptoid-peptide hybrids of the current invention of the invention in combination with a pharmaceutically acceptable carrier. Pharmaceutical compositions adapted for oral, topical or parenteral administration, comprising an amount of a compound constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, peptoids or peptoid-peptide hybrids of the current invention and compositions containing them contemplated by the present invention can be administered to a subject in need of treatment prior to, subsequent to, or in combination with other anti-cancer agents or treatments (e.g., chemotherapeutic agents, immunotherapeutic agents, radiotherapeutic agents, cytotoxic agents, etc.) and/or with radiation therapy and/or with surgical treatment to remove a tumor. For example, compounds and compositions of the present invention can be used in methods of treating cancer wherein the subject is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments may be given at the same as or at different times from the compounds of this invention. Examples of other chemotherapeutic agents contemplated within the scope of the invention include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafururacil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of immunotherapeutic agents contemplated within the scope of the invention include, but are not limited to, alemtuzumab, cetuximab (ERBITUX), gemtuzumab, iodine 131 tositumomab, rituximab, trastuzumab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) The subject invention also concerns methods for treating an oncological disorder comprising administering an effective amount of a compound and/or agent of the invention prior to, subsequent to, and/or in combination with administration of an anti-cancer agent, such as a chemotherapeutic agent, an immunotherapeutic agent, a radiotherapeutic agent, or radiotherapy.

Examples of some anti-cancer agents that can be used according to the present invention are listed in Table 3.

TABLE 3

Examples of Anti-Cancer Agents

| | |
|---|---|
| 13-cis-Retinoic Acid | Mylocel |
| 2-Amino-6-Mercaptopurine | Letrozole |
| 2-CdA | Neosar |
| 2-Chlorodeoxyadenosine | Neulasta |
| 5-fluorouracil | Neumega |
| 5-FU | Neupogen |
| 6-TG | Nilandron |
| 6-Thioguanine | Nilutamide |
| 6-Mercaptopurine | Nitrogen Mustard |
| 6-MP | Novaldex |
| Accutane | Novantrone |
| Actinomycin-D | Octreotide |
| Adriamycin | Octreotide acetate |
| Adrucil | Oncospar |
| Agrylin | Oncovin |
| Ala-Cort | Ontak |
| Aldesleukin | Onxal |
| Alemtuzumab | Oprevelkin |
| Alitretinoin | Orapred |
| Alkaban-AQ | Orasone |
| Alkeran | Oxaliplatin |
| All-transretinoic acid | Paclitaxel |
| Alpha interferon | Pamidronate |
| Altretamine | Panretin |
| | Paraplatin |

TABLE 3-continued

Examples of Anti-Cancer Agents

| | |
|---|---|
| Amethopterin | Pediapred |
| Amifostine | PEG Interferon |
| Aminoglutethimide | Pegaspargase |
| Anagrelide | Pegfilgrastim |
| Anandron | PEG-INTRON |
| Anastrozole | PEG-L-asparaginase |
| Arabinosylcytosine | Phenylalanine Mustard |
| Ara-C | Platinol |
| Aranesp | Platinol-AQ |
| Aredia | Prednisolone |
| Arimidex | Prednisone |
| Aromasin | Prelone |
| Arsenic trioxide | Procarbazine |
| Asparaginase | PROCRIT |
| ATRA | Proleukin |
| Avastin | Prolifeprospan 20 with Carmustine implant |
| BCG | Purinethol |
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | Rubex |
| Bleomycin | Rubidomycin hydrochloride |
| Bortezomib | Sandostatin |
| Busulfan | Sandostatin LAR |
| Busulfex | Sargramostim |
| C225 | Solu-Cortef |
| Calcium Leucovorin | Solu-Medrol |
| Campath | STI-571 |
| Camptosar | Streptozocin |
| Camptothecin-11 | Tamoxifen |
| Capecitabine | Targretin |
| Carac | Taxol |
| Carboplatin | Taxotere |
| Carmustine | Temodar |
| Carmustine wafer | Temozolomide |
| Casodex | Teniposide |
| CCNU | TESPA |
| CDDP | Thalidomide |
| CeeNU | Thalomid |
| Cerubidine | TheraCys |
| cetuximab | Thioguanine |
| Chlorambucil | Thioguanine Tabloid |
| Cisplatin | Thiophosphoamide |
| Citrovorum Factor | Thioplex |
| Cladribine | Thiotepa |
| Cortisone | TICE |
| Cosmegen | Toposar |
| CPT-11 | Topotecan |
| Cyclophosphamide | Toremifene |
| Cytadren | Trastuzumab |
| Cytarabine | Tretinoin |
| Cytarabine liposomal | Trexall |
| Cytosar-U | Trisenox |
| Cytoxan | TSPA |
| Dacarbazine | VCR |
| Dactinomycin | Velban |
| Darbepoetin alfa | Velcade |
| Daunomycin | VePesid |
| Daunorubicin | Vesanoid |
| Daunorubicin hydrochloride | Viadur |
| | Vinblastine |
| Daunorubicin liposomal | Vinblastine Sulfate |
| DaunoXome | Vincasar Pfs |
| Decadron | Vincristine |
| Delta-Cortef | Vinorelbine |
| Deltasone | Vinorelbine tartrate |
| Denileukin diftitox | VLB |
| DepoCyt | VP-16 |
| Dexamethasone | Vumon |
| Dexamethasone acetate | Xeloda |
| dexamethasone sodium phosphate | Zanosar |
| | Zevalin |
| Dexasone | Zinecard |
| Dexrazoxane | Zoladex |
| DHAD | Zoledronic acid |
| DIC | Zometa |

TABLE 3-continued

Examples of Anti-Cancer Agents

| | |
|---|---|
| Diodex | Gliadel wafer |
| Docetaxel | Glivec |
| Doxil | GM-CSF |
| Doxorubicin | Goserelin |
| Doxorubicin liposomal | granulocyte-colony stimulating factor |
| Droxia | Granulocyte macrophage colony stimulating factor |
| DTIC | |
| DTIC-Dome | Halotestin |
| Duralone | Herceptin |
| Efudex | Hexadrol |
| Eligard | Hexalen |
| Ellence | Hexamethylmelamine |
| Eloxatin | HMM |
| Elspar | Hycamtin |
| Emcyt | Hydrea |
| Epirubicin | Hydrocort Acetate |
| Epoetin alfa | Hydrocortisone |
| Erbitux | Hydrocortisone sodium phosphate |
| Erwinia L-asparaginase | Hydrocortisone sodium succinate |
| Estramustine | Hydrocortone phosphate |
| Ethyol | Hydroxyurea |
| Etopophos | Ibritumomab |
| Etoposide | Ibritumomab Tiuxetan |
| Etoposide phosphate | Idamycin |
| Eulexin | Idarubicin |
| Evista | Ifex |
| Exemestane | IFN-alpha |
| Fareston | Ifosfamide |
| Faslodex | IL-2 |
| Femara | IL-11 |
| Filgrastim | Imatinib mesylate |
| Floxuridine | Imidazole Carboxamide |
| Fludara | Interferon alfa |
| Fludarabine | Interferon Alfa-2b (PEG conjugate) |
| Fluoroplex | Interleukin-2 |
| Fluorouracil | Interleukin-11 |
| Fluorouracil (cream) | Intron A (interferon alfa-2b) |
| Fluoxymesterone | Leucovorin |
| Flutamide | Leukeran |
| Folinic Acid | Leukine |
| FUDR | Leuprolide |
| Fulvestrant | Leurocristine |
| G-CSF | Leustatin |
| Gefitinib | Liposomal Ara-C |
| Gemcitabine | Liquid Pred |
| Gemtuzumab ozogamicin | Lomustine |
| Gemzar | L-PAM |
| Gleevec | L-Sarcolysin |
| Lupron | Meticorten |
| Lupron Depot | Mitomycin |
| Matulane | Mitomycin-C |
| Maxidex | Mitoxantrone |
| Mechlorethamine | M-Prednisol |
| Mechlorethamine Hydrochlorine | MTC |
| | MTX |
| Medralone | Mustargen |
| Medrol | Mustine |
| Megace | Mutamycin |
| Megestrol | Myleran |
| Megestrol Acetate | Iressa |
| Melphalan | Irinotecan |
| Mercaptopurine | Isotretinoin |
| Mesna | Kidrolase |
| Mesnex | Lanacort |
| Methotrexate | L-asparaginase |
| Methotrexate Sodium | LCR |
| Methylprednisolone | |

Depending upon the disorder or disease condition to be treated, a suitable dose(s) may be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound and/or agent can be continuous or at distinct intervals, as can be determined by a person of ordinary skill in the art.

To provide for the administration of such dosages for the desired therapeutic treatment, in some embodiments, pharmaceutical compositions of the invention can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The subject invention also concerns kits comprising a composition comprising peptoids or peptoid-peptide hybrids of the current invention or composition of the invention in one or more containers. Kits of the invention can optionally include pharmaceutically acceptable carriers and/or diluents. In one embodiment, a kit of the invention includes one or more other components, adjuncts, or adjuvants as described herein. In another embodiment, a kit includes one or more anti-cancer agents, such as those agents described herein. In one embodiment, a kit of the invention includes instructions or packaging materials that describe how to administer a compound or composition of the kit. Containers of the kit can be of any suitable material, e.g., glass, plastic, metal, etc., and of any suitable size, shape, or configuration. In one embodiment, a compound or composition of the invention is provided in the kit as a solid, such as a tablet, pill, or powder form. In another embodiment, a compound or composition of the invention is provided in the kit as a liquid or solution. In one embodiment, the kit comprises an ampoule or syringe containing a compound and/or agent of the invention in liquid or solution form. A kit of the invention can also optionally comprise, in addition to a peptoid or peptoid-peptide hybrid of the current invention, or composition of the invention, one or more other anticancer agents, such as chemotherapeutic agents.

Mammalian species which benefit from the disclosed methods include, but are not limited to, primates, such as humans, apes, chimpanzees, orangutans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient" and "subject" are used interchangeably and are intended to include such human and non-human species. Likewise, in vitro methods of the present invention can be carried out on cells of such human and non-human species.

"Peptoids or peptoid-peptide hybrids of the current invention" refers to stapled peptoids and stapled peptoid-peptide of the invention. Furthermore, references to compounds and agents of the invention include the peptoids or peptoid-peptide hybrids described herein.

EXEMPLIFIED EMBODIMENTS

Embodiment 1

A stapled peptoid comprising a plurality of N-substituted glycines, wherein at least two of the N-substituted glycines are linked to each other by an intramolecular cross-link between the N-substitutions, and wherein the length and geometry of the cross-link pre-organizes the peptoid into a desired conformation.

Embodiment 2

A stapled peptoid-peptide hybrid comprising a plurality of amino acids and a plurality of N-substituted glycines, wherein at least two residues from the plurality of amino acids and the plurality of N-substituted glycines are linked to each other by an intramolecular cross-link, and wherein the length and geometry of the intramolecular cross-link provides stability to the peptoid-peptide hybrid.

Embodiment 3

The stapled peptoid-peptide hybrid of embodiment 2, wherein two N-substituted glycine residues or two amino acid residues are linked to each other by the intramolecular cross-link.

Embodiment 4

The stapled peptoid-peptide hybrid of embodiment 2, wherein an N-substituted glycine residue is linked to an amino acid residue by the intramolecular cross-link.

Embodiment 5

The stapled peptoid-peptide hybrid of embodiment 2, wherein the peptoid-peptide hybrid is a cyclic peptoid-peptide hybrid, the cyclic peptoid-peptide hybrid comprising a plurality of alternating peptoid-peptide sequences, wherein the peptoid-peptide sequences form at least two antiparallel beta-strands.

Embodiment 6

The stapled peptoid-peptide hybrid of embodiment 2, further comprising substitutions on the amino acid side chains or the N-substitutions on glycines, wherein the substitutions further stabilize the peptoid-peptide hybrids.

Embodiment 7

The stapled peptoid-peptide hybrid of any preceding embodiment, wherein one or more of the substitutions are selected from the groups listed in Table 1 or shown in FIG. 9, and wherein the substitutions may be the same or different.

Embodiment 8

The stapled peptoid-peptide hybrid of embodiment 2, wherein the peptoid-peptide hybrid is selected from formula I, formula II, formula III, formula IV, formula V, formula VI, formula VII, formula VIII, formula IX, formula X, formula XI, or formula XII.

Embodiment 9

The stapled peptoid-peptide hybrid of embodiment 8, wherein one or more of the R groups are selected from the groups listed in Table 1 or shown in FIG. 9.

Embodiment 10

The stapled peptoid-peptide hybrid of embodiment 2, wherein the peptoid-peptide hybrid is that of FIG. 1A, optionally including the attached linker, or optionally including the attached linker and resin.

Embodiment 11

The stapled peptoid-peptide hybrid of embodiment 10, wherein one or more of the R groups ($R_1$, $R_2$, $R_3$, or $R_4$) are selected from the groups listed in Table 1 or shown in FIG. 9.

Embodiment 12

The stapled peptoid-peptide hybrid of embodiment 2, wherein the peptoid-peptide hybrid is that of FIG. 1B or 1C.

Embodiment 13

The stapled peptoid-peptide hybrid of embodiment 2, wherein the peptoid-peptide hybrid is that of FIG. 3, FIG. 4, FIG. 5, or FIG. 6.

Embodiment 14

The stapled peptoid-peptide hybrid of embodiment 13, wherein one or more of the variable side chains are selected from the groups listed in Table 1 or shown in FIG. 9.

Embodiment 15

Figure 7:
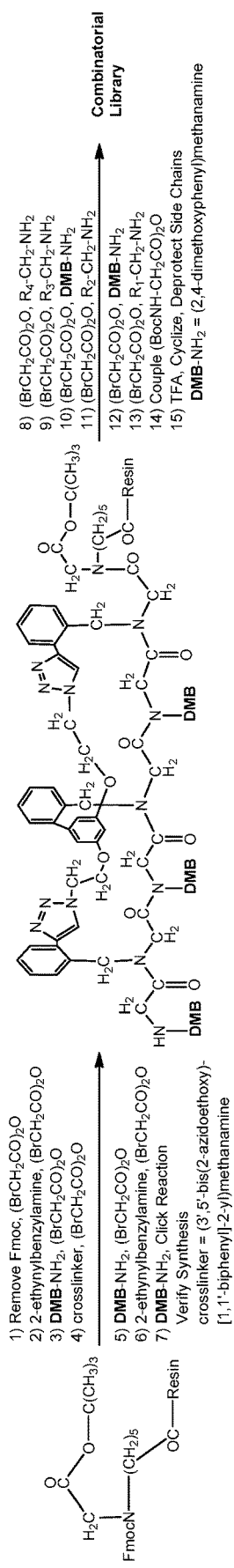
FIG. 7. Example of a reaction scheme for synthesis of a stapled peptoid-peptide with a cross-linker.

The stapled peptoid-peptide hybrid of embodiment 2, wherein the peptoid-peptide hybrid is that of FIG. 7 or FIG. 8, optionally including the attached resin.

Embodiment 16

A positional library of the peptoid-peptide hybrid of any preceding embodiment.

Embodiment 17

A method of positional library scanning for identification of a peptoid or a peptoid-peptide hybrid having a desired biological activity, the method comprising:

a. producing a library of the peptoids having a core peptoid structure or the peptoid-peptide hybrids having a core peptoid-peptide structure, wherein the library consists of compounds having various combinations of N number of possible side chains on X number of possible substitution positions on the core peptoid or the core peptoid-peptide hybrid, b. producing a positional scanning library comprising an array of spots containing the peptoids or the peptoid-peptide hybrids, c. conducting an assay for the desired biological activity to identify one or more spots on the positional scanning library that display the desired biological activity, and d. further testing the compounds present in the spots that display the desired biological activity to identify any compounds having the desired biological activity.

Embodiment 18

The method of embodiment 17, wherein the desired biological activity is a specific interaction with a biomolecule.

Embodiment 19

The method of embodiment 18, wherein the biomolecule is selected from a polypeptide (e.g., protein) or a nucleic acid molecule (e.g., DNA or RNA).

Embodiment 20

The method of any one of embodiment 17-19, wherein the library of peptoids comprises one or more from embodiment 1 to 15.

Embodiment 21

A method for the analysis of a library of peptoid-peptide hybrids to identify a peptoid-peptide hybrid capable of binding to one or more biomolecules (for example, proteins in or on a cell), comprising the steps of:

a) providing an array comprising a combinatorial peptoid-peptide library, b) providing a first cell expressing one or more biomolecules of interest, wherein the first cell is labeled with a first label, c) providing a second cell not expressing the one or more biomolecules of interest, wherein the second cell is labeled with a second label distinguishable from the first label, d) contacting the first cell and the second cell to the combinatorial peptoid-peptide library, e) identifying, from the combinatorial peptoid-peptide library, the peptoid-peptide hybrid capable of binding to one or more biomolecules as indicated by the presence of the first label and the absence of the second label on the one or more positions on the array corresponding to the peptoid-peptide hybrid molecules.

Embodiment 22

The method of embodiment 21, further comprising the step of labeling the first cell with the first label, and/or labeling the second cell with the second label.

Embodiment 23

The method of embodiment 20 or 21, wherein the biomolecule is a protein, nucleotide, lipid, or polysaccharide.

Embodiment 24

The method of any one of embodiments 20 to 23, wherein the biomolecule is a cytoplasmic protein or a cell surface protein (e.g., a cell surface receptor).

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Example 1: Positional Scanning with 69 Different Substituents

In an embodiment of the current invention, a molecular library displaying a mixture of 69 compounds having various substituents (listed in Table 1 or FIG. 9, for example) in either the $R_1$, or $R_2$, $R_3$ positions is prepared where all of the remaining R positions, e.g., $R_1$ and $R_2$, or $R_1$ and $R_3$, or $R_2$ and $R_3$ positions display each of the possible 69×69 combinations. This equals 69×69×3, i.e. 14,283 different spots. This number is much less than having to make every possible combination of 69×69×69, i.e. 328,509 spots which would have required 952.2 plates with 345 spots per plate. The positional scanning approach only requires 41.4 plates. A mixture of more compounds may also be utilized (e.g., 96 compounds instead of 69 compounds). It will be appreciated that additional R positions can be present, e.g., $R_4$, $R_5$, and $R_6$.

In this embodiment of the positional scanning approach, only about $1/69^{th}$ of a pure substance is displayed per spot. When a screen finds a hit, the hit is prepared anew to verify its activity. This approach gives ~1.4% of a particular sequence represented per well and by comparing with hits from other plates that discretely display the side chains in each of the three side chains the preferred side chains can be determined.

TABKE 1

Examples of substituents at $R_1$, $R_2$, or $R_3$ positions (or other R positions, e.g., $R_4$, $R_5$, $R_6$):

| | |
|---|---|
| 1 | $H_2N-CH_2-CH_2-CH_3$ |
| 2 | $H_2N-CH_2-CH_2-CH_2-CH_3$ |
| 3 | $H_2N-CH_2-CH(CH_3)_2$ |
| 4 | $H_2N-CH_2-CH_2-CH(CH_3)_2$ |
| 5 | $H_2N-CH_2$-CYCLOPENTYL |
| 6 | $H_2N-CH_2-CH_2$-CYCLOPENTYL |
| 7 | $H_2N-CH_2$-CYCLOHEXYL |
| 8 | $H_2N-CH_2-CH_2$-CYCLOHEXYL |
| 9 | $H_2N-CH_2$-PHENYL |
| 10 | $H_2N-CH_2-CH_2$-PHENYL |
| 11 | $H_2N-CH_2-CH_2-CH_2$-PHENYL |
| 12 | $H_2N-CH_2$-(1-NAPHTHYL) |
| 13 | $H_2N-CH_2-CH_2$-(1-NAPHTHYL) |
| 14 | $H_2N-CH_2-CH_2-CH_2$-(1-NAPHTHYL) |
| 15 | $H_2N-CH_2$-(2-NAPHTHYL) |
| 16 | $H_2N-CH_2-CH_2$-(2-NAPHTHYL) |
| 17 | $H_2N-CH_2-CH_2-CH_2$-(2-NAPHTHYL) |

TABKE 1-continued

Examples of substituents at $R_1$, $R_2$, or $R_3$ positions (or other R positions, e.g., $R_4$, $R_5$, $R_6$):

| | |
|---|---|
| 18 | $H_2N—CH_2$-(4-HYDROXYPHENYL)-(TERT-BUTYL PROTECTED) |
| 19 | $H_2N—CH_2—CH_2$-(4-HYDROXYPHENYL)-(TERT-BUTYL PROTECTED) |
| 20 | $H_2N—CH_2—CH_2—CH_2$-(4-HYDROXYPHENYL)-(TERT-BUTYL PROTECTED) |
| 21 | $H_2N—CH_2$-(4-METHOXYPHENYL) |
| 22 | $H_2N—CH_2—CH_2$-(4-METHOXYPHENYL) |
| 23 | $H_2N—CH_2—CH_2—CH_2$-(4-METHOXYPHENYL) |
| 24 | $H_2N—CH_2$-(4-CHLOROPHENYL) |
| 25 | $H_2N—CH_2—CH_2$-(4-CHLOROPHENYL) |
| 26 | $H_2N—CH_2—CH_2—CH_2$-(4-CHLOROPHENYL) |
| 27 | $H_2N—CH_2$-(3-HYDROXYPHENYL)-(TERT-BUTYL PROTECTED) |
| 28 | $H_2N—CH_2—CH_2$-(3-HYDROXYPHENYL)-(TERT-BUTYL PROTECTED) |
| 29 | $H_2N—CH_2—CH_2—CH_2$-(3-HYDROXYPHENYL)-(TERT-BUTYL PROTECTED) |
| 30 | $H_2N—CH_2$-(3-METHOXYPHENYL) |
| 31 | $H_2N—CH_2—CH_2$-(3-METHOXYPHENYL) |
| 32 | $H_2N—CH_2—CH_2—CH_2$-(3-METHOXYPHENYL) |
| 33 | $H_2N—CH_2$-(3-CHLOROPHENYL) |
| 34 | $H_2N—CH_2—CH_2$-(3-CHLOROPHENYL) |
| 35 | $H_2N—CH_2—CH_2—CH_2$-(3-CHLOROPHENYL) |
| 36 | $H_2N—CH_2—CH_2—OCH_3$ |
| 37 | $H_2N—CH_2—CH_2—CH_2—OCH_3$ |
| 38 | $H_2N—CH_2—CH_2—OH$(TERT-BUTYL PROTECTED) |
| 39 | $H_2N—CH_2—CH_2—CH_2—OH$(TERT-BUTYL PROTECTED) |
| 40 | $H_2N—CH_2$-(3-OXETANE) |
| 41 | $H_2N—CH_2—CH_2$-(3-OXETANE) |
| 42 | $H_2N—CH_2$-4-PYRAN |
| 43 | $H_2N—CH_2—CH_2$-(4-PYRAN) |
| 44 | $H_2N—CH_2—COOH$(TERT-BUTYL PROTECTED) |
| 45 | $H_2N—CH_2—CH_2—COOH$(TERT-BUTYL PROTECTED) |
| 46 | $H_2N—CH_2$-PHENYL-4-COOH(TERT-BUTYL PROTECTED) |
| 47 | $H_2N—CH_2—CH_2$-PHENYL-4-COOH(TERT-BUTYL PROTECTED) |
| 48 | $H_2N—CH_2—CO—NHCH_3$(PROTECTED) |
| 49 | $H_2N—CH_2—CH_2—CO—NHCH_3$ |
| 50 | $H_2N—CH_2$-PHENYL-4-CO—$NHCH_3$ |
| 51 | $H_2N—CH_2—CH_2$-PHENYL-4-CO—$NHCH_3$ |
| 52 | $H_2N—CH_2—CO—N(CH_3)_2$ |
| 53 | $H_2N—CH_2—CH_2—CO—N(CH_3)_2$ |
| 54 | $H_2N—CH_2$-PHENYL-4-CO—$N(CH_3)_2$ |
| 55 | $H_2N—CH_2—CH_2$-PHENYL-4-CO—$N(CH_3)_2$ |
| 56 | $H_2N—CH_2—CH_2—NH_2$(BOC PROTECTED) |
| 57 | $H_2N—CH_2—CH_2—CH_2—NH_2$(BOC PROTECTED) |
| 58 | $H_2N—CH_2—CH_2—NH—COCH_3$ |
| 59 | $H_2N—CH_2—CH_2—CH_2—NH—COCH_3$ |
| 60 | $H_2N—CH_2—CH_2$-MORPHOLINE |
| 61 | $H_2N—CH_2—CH_2—CH_2$-MORPHOLINE |
| 62 | $H_2N—CH_2$-2-IMIDAZOLE(BOC PROTECTED) |
| 63 | $H_2N—CH_2—CH_2$-2-IMIDAZOLE(BOC PROTECTED) |
| 64 | $H_2N—CH_2—CH_2—CH_2$-2-IMIDAZOLE(BOC PROTECTED) |
| 65 | $H_2N—CH_2—CH_2—N=C(NH_2)_2$(BOC PROTECTED) |
| 66 | $H_2N—CH_2—CH_2—CH_2—N=C(NH_2)_2$(BOC PROTECTED) |
| 67 | $H_2N—CH_2—CH_2—CH_2—CH_2—N=C(NH_2)_2$(BOC PROTECTED) |
| 68 | $H_2N—CH_2—CH_2—CH_2—CH_2—CH_2—N=C(NH_2)_2$(BOC PROTECTED) |
| 69 | $H_2N—CH_2—CH_2$-(3-INDOLYL) |

Figure 2:
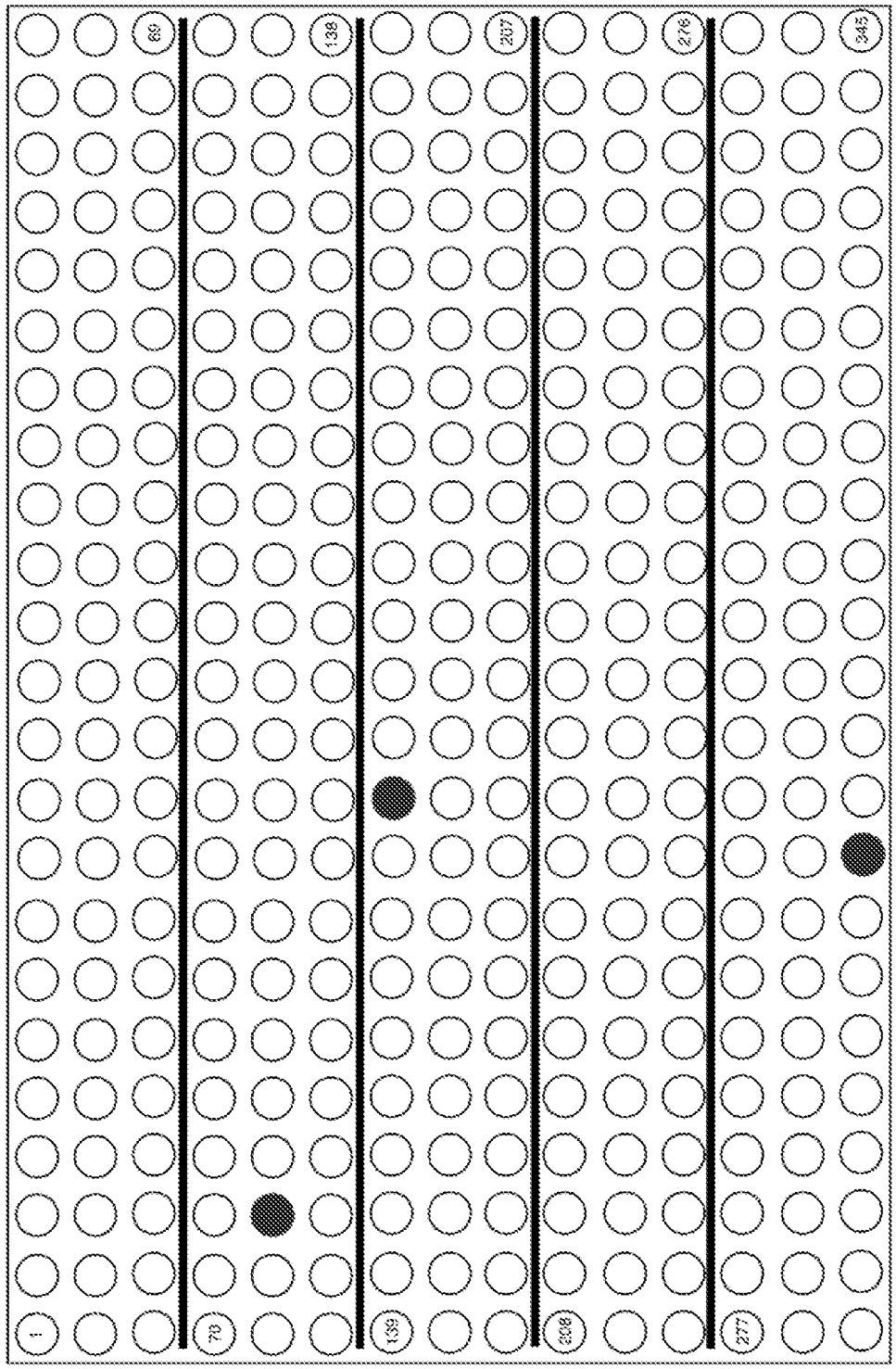
FIG. 2. Example of positional library scanning plate.

FIG. 2 is an example of a plate used for positional scanning. Spots 1-69 would have the $R_1$ identical in all the spots and each of the individual and different 69 side chains in the $R_2$ and a mixture of all 69 compounds displayed in the $R_3$ position. Spots 70-138 would analogously have all the $R_1$ positions displaying side chain 2 and then each of the 69 different side chains in the $R_2$ position and a mixture of 69 different side chains displayed in the $R_3$ position and so on to cover all possible combinations. The specific $R_2$ plates would have a mixture of 69 compounds displayed in the $R_1$ position and then all of the 69 spots with the $R_2$ having the same side chain equal to compound 1 and then each individual 69 compounds for the $R_3$ analogous to the $R_1$ specific plates described above then the remaining combination where the $R_1$ position will display each of the 69, the $R_2$ will display the mixture of the 69 compounds, and spots 1-69 will all have the same side chain at the $R_3$ position.

An example of the results of the positional screening is also shown in FIG. 2. The first shaded spot has the best $R_1$ side chains with the side chain equal to compound 2 and $R_2$ is equal to compound 26, and at least one of the 69 possible compounds in position $R_3$. The next spot shows that compound 3 is active in $R_1$ and $R_2$ has compound 10 and at least one of the 69 compounds in position $R_3$. The last spot on the plate shows that $R_1$ equals to compound 5 and compound 55 for $R_2$ and at least one of the 69 compounds in position $R_3$. By analyzing the analogous screening results from the defined $R_2$ and $R_3$ position plates the exact sequence can be determined.

69 compounds with similar reactivity in the SN2 reaction to make the secondary amines are needed. Enormous structurally variability is possible, but some examples of potential side chains are shown in Table 1 and FIG. 9.

Figure 3:
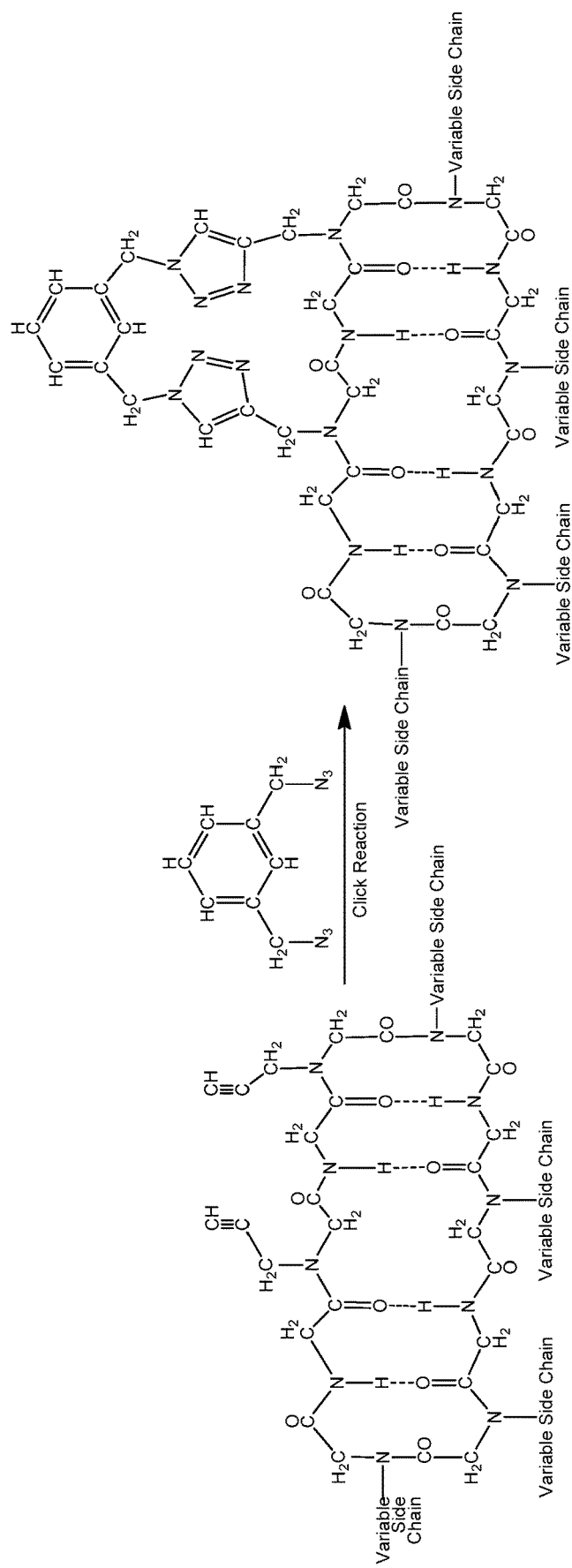
FIG. 3. Example of a reaction scheme to stabilize the cyclic beta-hairpin-like peptoid-peptide hybrid scaffold using a meta-xylenyl group.

Example 2: Stapling Methods to Stabilize the Cyclic Beta-Hairpin-Like Peptoid-Peptide Hybrid Scaffold There are several viable stapling methods that may be used to stabilize the cyclic beta-hairpin-like peptoid-peptide hybrid scaffold. The stapling of two peptoid side chains is the easiest to accomplish from a synthetic point of view and will pre-organize those two peptoid side chains to be proximate to each other, and that proximity enforces conformations of the overall scaffold that are compatible with the desired cyclic beta-hairpin-like secondary structure. The easiest pairs to staple are propargyl amines in the peptoid side chains to be stapled and to react those two terminal alkynes with a bifunctional diazide with a stable organic linker that spans the distance between those peptoid side chains. The organic linker needs 3 more atoms to span that distance. The meta-xylenyl group is shown in FIG. 3; however, any stable combination of atoms may be used. In addition, the chain need not be just a linker, as the group could also be used to optimize pharmacokinetics properties, for example.

Figure 4:
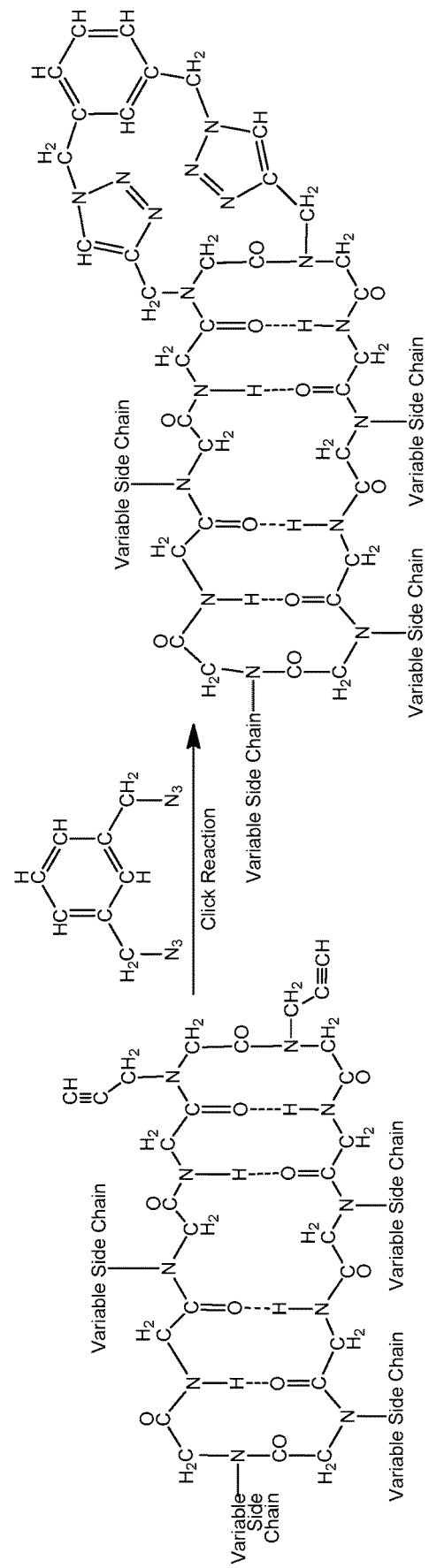
FIG. 4. Example of a reaction scheme to stabilize the cyclic beta-hairpin-like peptoid-peptide hybrid scaffold, by stapling propargyl side chains that are on more proximate peptide side chains.
Figure 5:
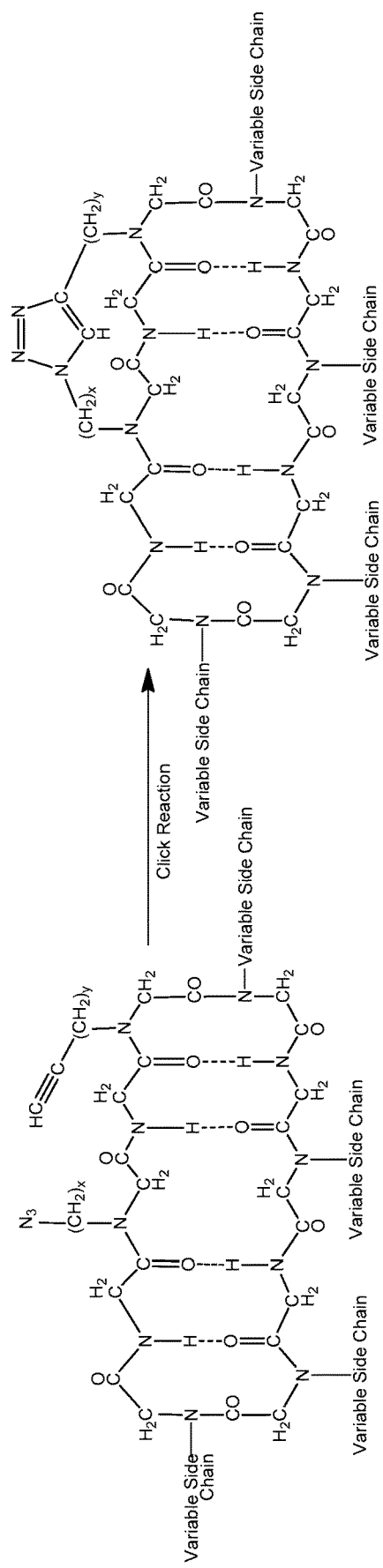
FIG. 5. Example of a reaction scheme to stabilize the cyclic beta-hairpin-like peptoid-peptide hybrid scaffold using an azide and an alkyne.
Figure 6:
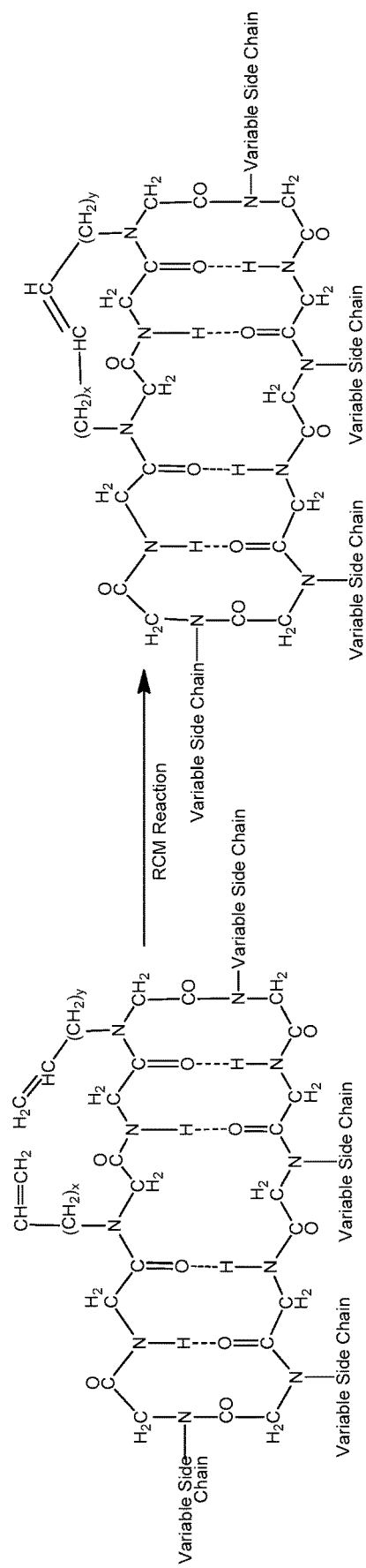
FIG. 6. Example of a reaction scheme to stabilize the cyclic beta-hairpin-like peptoid-peptide hybrid scaffold using ring closing metathesis (RCM).

Alternatively, the same or a different linker can be used to staple propargyl side chains that are on more proximate peptoid side chains, as shown in FIG. 4. As described herein, a side chain from an amino acid side and a proximate peptoid side chain are also possible, but not shown. A more generic scheme that uses an azide and an alkyne is shown in FIG. 5. The RCM (Ring Closing Metathesis) reaction may also be used, as shown by the generic example in FIG. 6.

We claim:

1. A method of positional library scanning for identification of a peptoid or a peptoid-peptide hybrid having a desired biological activity, the method comprising:
   a. producing a library of the peptoids having a core peptoid structure or the peptoid-peptide hybrids having a core peptoid-peptide structure, wherein the library consists of compounds having various combinations of possible side chains on a number of possible substitution positions on the core peptoid or the core peptoid-peptide hybrid,
   wherein each peptoid comprises a plurality of N-substituted glycines, wherein at least two of the N-substituted glycines are linked to each other by an intramolecular cross-link between the N-substitutions, and wherein the length and geometry of the cross-link pre-organizes the peptoid into a desired conformation, and wherein each peptoid-peptide hybrid comprises a plurality of amino acids and a plurality of N-substituted glycines, wherein at least two residues from the plurality of amino acids and the plurality of N-substituted glycines are linked to each other by an intramolecular cross-link, and wherein the length and geometry of the intramolecular cross-link provides stability to the peptoid-peptide hybrid, b. producing a positional scanning library comprising an array of spots containing the peptoids or the peptoid-peptide hybrids, c. conducting an assay for the desired biological activity to identify one or more spots on the positional scanning library that display the desired biological activity, and d. further testing the compounds present in the spots that display the desired biological activity to identify the compounds having the desired biological activity.

2. The method of claim 1, wherein the desired biological activity is a specific interaction with a biomolecule.

3. The method of claim 2, wherein the biomolecule is selected from a polypeptide or a nucleic acid molecule.

4. The method of claim 1, wherein the library of peptoids comprises one or more stabled peptoids comprising a plurality of N-substituted glycines, wherein at least two of the N-substituted glycines are linked to each other by an intramolecular cross-link between the N-substitutions, and wherein the length and geometry of the cross-link pre-organizes the peptoid into a desired conformation.

5. The method of claim 1, wherein the library of peptoids comprises one or more stapled peptoid-peptide hybrids comprising a plurality of amino acids and a plurality of N-substituted glycines, wherein at least two residues from the plurality of amino acids and the plurality of N-substituted glycines are linked to each other by an intramolecular cross-link, and wherein the length and geometry of the intramolecular cross-link provides stability to the peptoid-peptide hybrid.

6. A method for the analysis of a library of peptoid-peptide hybrids to identify a peptoid-peptide hybrid capable of binding to one or more biomolecules, comprising the steps of:

a) providing an array comprising a combinatorial peptoid-peptide library, b) providing a first cell expressing one or more biomolecules of interest, wherein the first cell is labeled with a first label, c) providing a second cell not expressing the one or more biomolecules of interest, wherein the second cell is labeled with a second label distinguishable from the first label, d) contacting the first cell and the second cell to the combinatorial peptoid-peptide library, e) identifying, from the combinatorial peptoid-peptide library, the peptoid-peptide hybrid capable of binding to one or more biomolecules as indicated by the presence of the first label and the absence of the second label on the one or more positions on the array corresponding to the peptoid-peptide hybrid molecules wherein each peptoid-peptide hybrid comprises a plurality of amino acids and a plurality of N-substituted glycines, wherein at least two residues from the plurality of amino acids and the plurality of N-substituted glycines are linked to each other by an intramolecular cross-link, and wherein the length and geometry of the intramolecular cross-link provides stability to the peptoid-peptide hybrid.

7. The method of claim 6, wherein the one or more biomolecules comprise a protein, nucleotide, lipid, polysaccharide, or a combination thereof.

8. The method of claim 7, wherein the protein is a cytoplasmic protein or a cell surface protein.

9. The method of claim 8, wherein the cell surface protein comprises 41BB receptor and TNF-β receptor.

10. The method of claim 6, wherein the first label and the second label are a fluorescent label, a quantum dot label, a radiolabel, an enzyme label, a chromophore label, a chemiluminescent label, or an antibody label.

11. The method of claim 6, wherein the first label is a quantum dot of a first color and the second label is a quantum dot of a second color.

12. The method of claim 6, wherein the array comprising the peptoid-peptide library comprises spots of peptide-peptoid hybrids in the library on a solid support in a multi-well containing peptide-peptoid hybrids in the library.

* * * * *

UNITED STATES PATENT AND TRADEMARK OFFICE
CERTIFICATE OF CORRECTION

PATENT NO. : 10,556,928 B2
APPLICATION NO. : 16/157174
DATED : February 11, 2020
INVENTOR(S) : Mark McLaughlin and Amod A. Sarnaik Page 1 of 1

It is certified that error appears in the above-identified patent and that said Letters Patent is hereby corrected as shown below:

In the Specification

<u>Column 5,</u>

Lines 26-43, " 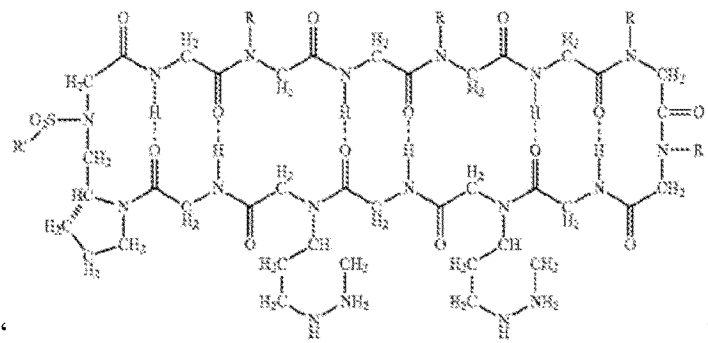 " should read

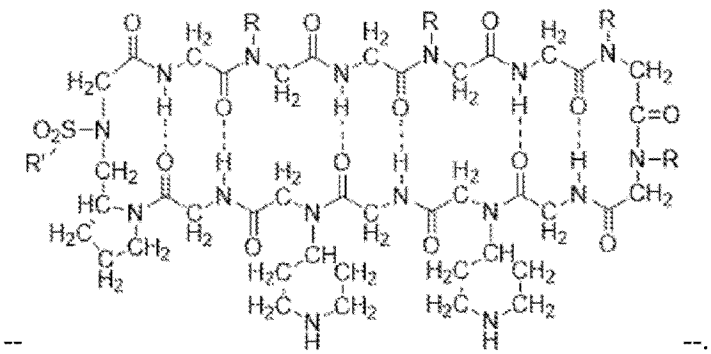

--         --.

Signed and Sealed this
Eighteenth Day of August, 2020

Andrei Iancu
*Director of the United States Patent and Trademark Office*